US008632773B2

(12) United States Patent
Käsermann et al.

(10) Patent No.: US 8,632,773 B2
(45) Date of Patent: Jan. 21, 2014

(54) ANTIBODY COMPOSITION WITH ALTERED FAB SIALYLATION

(75) Inventors: Fabian Käsermann, Burgdorf (CH); Monika Rüegsegger, Thun (CH); Sylvia Miescher, Bern (CH); Keith Elkon, Seattle, WA (US)

(73) Assignees: CSL Behring AG, Bern (CH); University of Washington, Seattle, WA (US)

( * ) Notice: Subject to any disclaimer, the term of this patent is extended or adjusted under 35 U.S.C. 154(b) by 0 days.

(21) Appl. No.: 13/260,202

(22) PCT Filed: Mar. 26, 2010

(86) PCT No.: PCT/US2010/028889
§ 371 (c)(1),
(2), (4) Date: Sep. 23, 2011

(87) PCT Pub. No.: WO2010/111633
PCT Pub. Date: Sep. 30, 2010

(65) Prior Publication Data
US 2012/0009189 A1 Jan. 12, 2012

(30) Foreign Application Priority Data
Mar. 26, 2009 (EP) .................................. 09004358

(51) Int. Cl.
A61K 39/395 (2006.01)
A61K 35/12 (2006.01)
A61K 35/14 (2006.01)
A61K 35/16 (2006.01)
C07K 16/00 (2006.01)

(52) U.S. Cl.
USPC ......... 424/130.1; 424/520; 424/529; 424/530

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. | |
| 6,080,560 A | 6/2000 | Russell et al. | |
| 6,656,466 B1 | 12/2003 | Etcheverry et al. | |
| 2008/0206246 A1* | 8/2008 | Ravetch et al. | 424/134.1 |

FOREIGN PATENT DOCUMENTS

| | | |
|---|---|---|
| CA | 2185617 A1 | 3/1997 |
| EP | 0 764 658 A1 | 3/1997 |
| EP | 1 394 183 A1 | 3/2004 |
| WO | WO 2005/016455 A2 | 2/2005 |
| WO | WO 2007/005786 A2 | 1/2007 |
| WO | WO 2007/055916 A2 | 5/2007 |
| WO | WO 2007/117505 A2 | 10/2007 |
| WO | WO 2008/057634 A2 | 5/2008 |
| WO | WO 2009/079382 A1 | 6/2009 |

OTHER PUBLICATIONS

Yildirim-Toruner et al. J. Allergy Clin. Immunol 2011;127:303-12.*
Arnal et al. The Journal of Rheumatology. 2002, 29;1:75-83.*
J.C. Roder et al., "Abstract 0106: Recent Advances in the EBV-hybridoma Technique," from *Monoclonal Antibodies and Cancer Therapy* (vol. 27, UCLA Symposia on Molecular and Cellular Biology, New Series) (eds. R.A. Reisfeld and S.Sell), Alan R. Liss, Inc. (1985), pp. 33 and 47.
M. Dalziel et al., "Lectin analysis of human immunoglobulin G N-glycan sialylation," Glycoconjugate J., 16: 801-807 (1999).
M. Jacquemin et al., "Variable region heavy chain glycosylation determines the anticoagulant activity of a factor VIII antibody," J. Thromb. Haemost., 4: 1047-1055 (2006).
R. Jefferis, "Glycosylation as a strategy to improve antibody-based therapeutics," Nature Reviews/Drug Discovery, 8: 226-234 (Mar. 2009).
Y. Kaneko et al., "Anti-Inflammatory Activity of Immunoglobulin G Resulting from Fc Sialytion," Science, 313: 670-673 (2006).
M. Kato et al., "Activity enhancement of a lung cancer-associated human monoclonal antibody HB4C5 by N-deglycosylation," Hum. Antibod. Hybridomas, 4: 9-14 (1993).
S. Khurana et al., "The Variable Domain Glycosylation in a Monoclonal Antibody Specific to GnRH Modulates Antigen Binding," Biochem. Biophys. Res. Comm., 234: 465-469 (1997).
N. Kinoshita et al., "Glycosylation at the Fab Portion of Myeloma Immunoglobulin G and Increased Fucosylated Biantennary Sugar Chains: Structural Analysis by High-Performance Liquid Chromatography and Antibody-Lectin Enzyme Immunoassay Using *Lens culnaris* Agglutinin," Cancer Res., 51: 5888-5892 (1991).
T. Millward et al., "Effect of constant and variable domain glycosylation on pharmacokinetics of therapeutic antibodies in mice," Biologicals, 36: 41-47 (2008).

(Continued)

*Primary Examiner* — Chun Dahle
(74) *Attorney, Agent, or Firm* — Finnegan, Henderson, Farabow, Garrett & Dunner, LLP

(57) ABSTRACT

The present invention relates to a population of antibodies enriched from an antibody preparation, wherein the enriched population of antibodies has an altered amount of sialylation in the Fab region of the antibodies as compared to the antibody preparation prior to enrichment. Furthermore, the present invention relates to a method of enriching a population of antibodies from an antibody preparation, wherein the enriched population of antibodies has an altered amount of sialylation in the Fab region of the antibodies as compared to the antibody preparation prior to enrichment. The present invention also relates to the population of antibodies of the invention for use in medicine, a pharmaceutical composition comprising the populations of antibodies of the invention and the use of the population of antibodies of the invention in the prevention and/or treatment of atherosclerosis, cancer and infections such as bacterial, viral or fungal infections.

6 Claims, 8 Drawing Sheets

(56) References Cited

OTHER PUBLICATIONS

Figure 1:
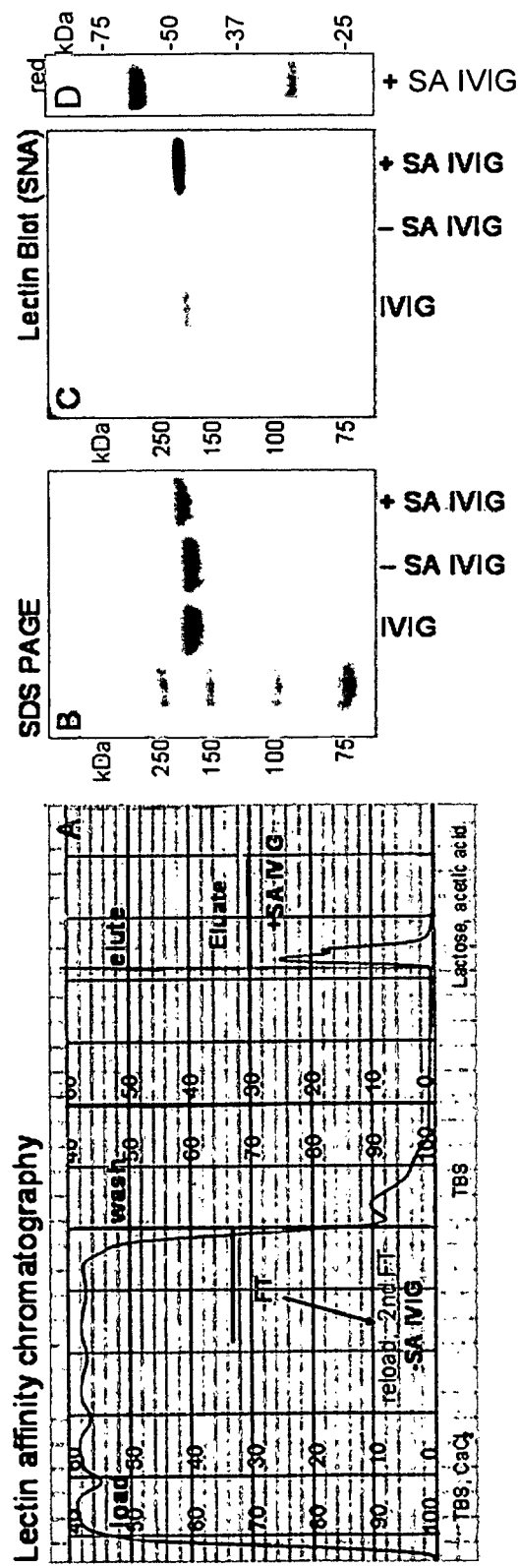

J.-F. Seite et al., "What is the contents of the magic draft IVIg?," Autoimmunity Reviews, 7: 435-439 (2008).
Vector Laboratories, Inc., "Sambucus Nigra Lectin (SNA, EBL)" from http://web.archive.org/web/20010509232352/http://vectorlabs.com/Lectins/LSNA.htm, Online May 9, 2011, retrieved Sep. 27, 2010 (1 page).
Notification of Transmittal of the International Search Report and the Written Opinion of the International Searching Authority, or the Declaration, for International Patent App. No. PCT/US2010/028889, mailed Nov. 19, 2010 (19 pages).
S. M. Andrew et al., "Section III: Purification and Fragmentation of Antibodies," from *Current Protocols in Immunology*, John Wiley & Sons, Inc., Supplement 21: 2.7.1-2.7.12 (1997).
S. M. Andrew et al., "Unit 2.8: Fragmentation of Immunoglobulin G," from *Current Protocols in Immunology*, John Wiley & Sons, Inc., Supplement 21: 2.8.1-2.8.10 (1997).
A. A. Bengtsson et al., "Activation of type I interferon system in systemic lupus erythematosus correlates with disease activity but not with antiretroviral antibodies," Lupus, (: 664-671 (2000).
P. A. Brady et al., "Selection approaches to catalytic systems," Chem. Soc. Rev., 26: 327-336 (1997).
S. L. Diaz et al., "Sensitive and Specific Detection of the Non-Human Sialic Acid N-Glycolylneuraminic Acid in Human Tissues and Biotherapeutic Products," PLoS One, 4(1): E4241 (10 pages) (2009).
Y. Echelard et al., "Toward a new cash cow: Cloned cattle engineered to carry an artificial chromosome encoding human immunoglobulin genes are a significant leap toward the production of safer and more potent therapeutic antibodies," Nature Biotech., 20: 881-882 (2002).
H. H. Freeze et al., "Unit 12.4: Endoglycosidase and Glycoamidase Release of N-Linked Glycans," from *Current Protocols in Protein Science*, John Wiley & Sons, Inc., Supplement 62: 12.4.1-12.4.25 (2010).
D. J. Harvey et al., "Unit 12.7: Determining the Structure of Glycan Moieties by Mass Spectrometry," from *Current Protocols in Protein Science*, John Wiley & Sons, Inc., Supplement 43: 12.7.1-12.7.18 (2006).
M. J. Huddleston et al., "Collisional Fragmentation of Glycopeptides by Electrospray Ionization LC/MS and LC/MS/MS: Methods for Selective Detection of Glycopeptides in Protein Digests," Anal. Chem., 65: 877-884 (1993).
R. Jefferis, "Glycosylation of Recombinant Antibody Therapeutics," Biotechnol. Prog., 21:11-16 (2006).
Kanamori et al., "Deaminated Neuraminic Acid-rich Glycoprotein of Rainbow Trout Egg Vitelline Envelope," J. Biol. Chem., 265(35): 21811-21819 (1990).
N. G. Karlsson et al., "Negative ion graphitized carbon nano-liquid chromatography/mass spectrometry increases sensitivity for glycoprotein oligosaccharide analysis," Rapid Comm. Mass. Spec., 18: 2282-2292 (2004).
G. Köhler et al., "Continuous cultures of fused cells secreting antibody of predefined specificity," Nature, 256: 495-497 (1975).
D. Kozbor et al., "The production of monoclonal antibodies from human lymphocytes," Immunol. Today, 4(3): 72-79 (1983).

J. P. Kunkel et al., Comparisons of the Glycosylation of a Monoclonal Antibody Produces under Nominally Identical Cell Culture conditions in Two Different Bioreactors,: Biotechnol. Prog., 16: 462-470 (2000).
C. T. Mant et al., "Mixed-mode hydrophilic interaction/cation-exchange chromatography (HILIC/CEX) of peptides and proteins," J. Sep. Sci., 31: 2754-2773 (2008).
A. Matsumoto et al., "Autoantibody Activity of IgG Rheumatoid Factor Increases with Decreasing Levels of Galactosylation and Sialylation," J. Biochem., 128: 621-628 (2000).
D. Nadano et al., A Naturally Occurring Deaminated Neuraminic Acid, 3-Deoxy-D-*glycero*-D-*galacto*-nonulosonic Acid (KDN), J. Biol. Chem., 261(25): 11550-11557 (1986).
A. Nicoletti et al., "Immunoglobulin Treatment Reduces Atherosclerosis in apo E Knockout Mice," J. Clin. Invest., 102(5): 910-918 (1998).
F. Nimmerjahn et al., "The antiinflammatory activity of IgG: the intravenous IgG paradox," J. Exp. Med., 204(1): 11-15 (2007).
R. B. Parekh et al., "Association of rheumatoid arthritis and primary osteoarthritis with changes in the glycosylation pattern of total serum IgG," Nature, 316: 452-457 (1985).
T. P. Patel et al., Different culture methods lead to differences in glycosylation of a murine IgG monoclonal antibody, Biochem. J., 285: 839-845 (1992).
S. Patterson et al., "Tuning the Affinity of a Synthetic Sialic Acid Receptor Using Combinatorial Chemistry," Tetrahedron Letters, 39: 3111-3114 (1998).
T. W. Rademacher et al., "Agalactosyl glycoforms of IgG autoantibodies are pathogenic," Proc. Natl. Acad. Sci. USA, 91: 6123-6127 (1994).
L. Royle et al., "Unit 12.6: Determining the Structure of Oligosaccharides N- and O-Linked to Glycoproteins," from *Current Protocols in Protein Science*, John Wiley & Sons, Inc., Supplement 43: 12.6.1-12.6.45 (2006).
D. M. Santer et al., "Potent Induction of IFN-α and Chemokines by Autoantibodies in the Cerebrospinal Fluid of Patients with Neuropsychiatric Lupus," J. Immunol., 182: 1192-1201 (2009).
W. C. Still, "Discovery of Sequence-Selective Peptide Binding by Synthetic Receptors Using Encoded combinatorial Libraries," Acc. Chem. Res., 29: 155-163 (1996).
D. H. Van Den Eijnden et al., "Detection of β-Galactosyl(1→4)N-acetylglucosaminide α(2→3)-Sialyltransferase Activity in Fetal Calf Liver and Other Tissues," J. Biol. Chem., 256(7): 3159-3162 (1981).
A. Varki, "Mini review: Diversity in the sialic acids," Glycobiology, 2(1): 25-40 (1992).
A. Varki, "Corrigendum: Diversity in the sialic acids," Glycobiology, 2(2): 169 (1992).
J. Vollmer et al., "Immune stimulation mediated by autoantigen binding sites within small nuclear RNAs involves Toll-like receptors 7 and 8," J. Exp. Med., 202(11): 1575-1585 (2005).
D. X. Wen et al., "Primary Structure of Galβ1,3(4)GlcNAc α2,3-Sialyltransferase Determined by Mass Spectrometry Sequence Analysis and Molecular Cloning," J. Biol. Chem., 267(29): 21011-21019 (1992).
Extended European Search Report, mailed Aug. 11, 2009, for EP Patent Application No. 09004358.9-2402 (9 pages).
Leontyev et al., "Sialylation-independent mechanism involved in the amelioration of murine immune thrombocytopenia using intravenous gammaglobulin," Transfusion, 52:1799-1805 (Aug. 2012).

* cited by examiner

| % of glycans / glycopeptides with one or more sialic acid | | | |
|---|---|---|---|
| Fraction | Total N-glycans | IgG1 Fc glycopeptides | IgG2/3 Fc glycopeptides |
| IVIG | 21.96 ±0.7 | 10.3 ±0.4 | 9.6 ±0.6 |
| +SA IVIG | 54.25 ±0.6 | 12.1 ±0.5 | 9.8 ±0.2 |
| -SA IVIG | 16.86 ±0.5 | 10.1 ±0.4 | 9.4 ±0.2 |
| F(ab')$_2$ from IVIG | 50.0 ±0.4 | | |
| F(ab')$_2$ from +SA IVIG | 84.5 ±0.4 | | |
| F(ab')$_2$ from -SA IVIG | 25.7 ±0.3 | | |

SEQUENCE LISTING

<160> NUMBER OF SEQ ID NOS: 4

<210> SEQ ID NO 1
<211> LENGTH: 9
<212> TYPE: PRT
<213> ORGANISM: Homo sapiens

<400> SEQUENCE: 1

Glu Glu Gln Tyr Asn Ser Thr Tyr Arg
1               5

<210> SEQ ID NO 2
<211> LENGTH: 25
<212> TYPE: PRT
<213> ORGANISM: Homo sapiens

<400> SEQUENCE: 2

-continued

```
Glu Glu Gln Phe Asn Ser Thr Phe Cys Val Val Ser Val Leu Thr Val
1               5                   10                  15

Val His Gln Asp Trp Leu Asn Gly Lys
                20                  25

<210> SEQ ID NO 3
<211> LENGTH: 9
<212> TYPE: PRT
<213> ORGANISM: Homo sapiens

<400> SEQUENCE: 3

Glu Glu Gln Tyr Asn Ser Thr Phe Arg
1               5

<210> SEQ ID NO 4
<211> LENGTH: 9
<212> TYPE: PRT
<213> ORGANISM: Homo sapiens

<400> SEQUENCE: 4

Glu Glu Gln Phe Asn Ser Thr Tyr Arg
1               5
```

ANTIBODY COMPOSITION WITH ALTERED FAB SIALYLATION

STATEMENT REGARDING FEDERALLY SPONSORED RESEARCH

This invention was made, in part, with government support under grant number RO1 NS065933-01 awarded by the National Institutes of Health. The government has certain rights in the invention.

CROSS REFERENCE TO RELATED APPLICATIONS

This application is a U.S. national phase application based on PCT/US2010/028889, filed Mar. 26, 2010, which claims priority to European Application No. 09 004 358.9, filed Mar. 26, 2009.

The invention relates to populations of antibodies with altered sialylation in the Fab region, methods of their preparation, and uses thereof.

BACKGROUND TO THE INVENTION

Immunoglobulins, also known as antibodies, are the major secretory products of the immune system. They are typically formed of basic structural units—each with 2 heavy chains and 2 light chains—to form monomers with one such unit, dimers with two units, pentamers with five units, or hexamers with six units. Antibodies play a significant role in innate immunity. In a natural immune response to a pathogen, complexes are formed between the pathogen and antibodies. These immune complexes activate a wide range of effector functions, thus leading to the killing, removal and destruction of the pathogen. Antibodies can also react with the body's own antigens, which can lead to autoimmune diseases, and contribute to chronic inflammatory symptoms. Antibodies can have an anti-inflammatory activity, for example by targeting and neutralising various mediators in the inflammatory cascade.

There are five major isotypes of immunoglobulins, which perform different roles. IgG provides the majority of antibody-based immunity against invading pathogens, and is discussed in more detail below. IgM occurs in a membrane-bound form and in solution. In solution, it typically forms a pentamer, providing high avidity in binding to the antigen. It is often the first, immediate defence against infections before sufficient specific IgG is produced. IgA usually occurs as a dimer and is found in mucosal areas, e.g. the gut, lung and urogenital tract. It protects these surfaces against colonization by pathogens. IgE is mainly involved in allergic reactions. It binds to allergens and triggers histamine release from mast cells and basophils. IgD is found mainly on the surface of B lymphocytes that have not been exposed to antigens.

In humans, four subclasses of IgGs are defined and numbered according to their relative concentrations in normal serum: IgG1, IgG2, IgG3 and IgG4, which respectively account for approximately 60%, 25%, 10% and 5% of serum IgG, each IgG subclass possessing unique effector functions.

In general, each individual monomeric immunoglobulin unit, e.g. an IgG molecule, consists of two identical light chains and two identical heavy chains, which in turn comprise repeating structural motifs of approximately 110 amino acid residues. Domains of the light and heavy chains pair in covalent and non-covalent associations, thus forming three independent protein moieties connected through a flexible linker, the so-called hinge region. Two of these moieties are referred to as Fab (antigen-binding fragment) regions and are of identical structure. Each of the Fab regions forms the same specific antigen-binding site. The third moiety is the Fc (crystallizable fragment) region, which forms interaction sites for ligands that activate clearance and transport mechanisms.

IgGs play an important role in diseases. IgG1-type antibodies are the most commonly used antibodies in cancer immunotherapy where antibody-dependent cell-mediated cytotoxicity (ADCC) is often deemed important. Furthermore, IgGs are known to mediate both pro- and anti-inflammatory activities through interactions mediated by their Fc fragments. On one hand, interactions between Fc and its respective receptors are responsible for the pro-inflammatory properties of immune complexes and cytotoxic antibodies. On the other hand, intravenous gamma globulin (IVIG) and its Fc fragments are anti-inflammatory and are widely used to suppress inflammatory diseases. The precise mechanism of such paradoxical properties is unclear but it has been proposed that glycosylation of IgG is crucial for regulation of cytotoxicity and inflammatory potential of IgG.

To date, research into the role of glycosylation in the regulation of cytotoxicity and the inflammatory effects mediated by IgGs has mainly focused on the Fc region. Glycosylation of IgG is essential for binding to all FcγRs by maintaining an open conformation of the two heavy chains. This requirement of IgG glycosylation for FcγR binding explains the inability of de-glycosylated IgG antibodies to mediate in vivo triggered inflammatory responses, such as antibody-dependent cell-mediated cytotoxicity (ADCC), phagocytosis and the release of inflammatory mediators. A link between autoimmune states and specific glycosylation patterns of IgG antibodies has been observed in patients with rheumatoid arthritis and several autoimmune vasculities in which decreased galactosylation and sialylation of IgG antibodies have been reported (Parekh et al., Nature 316, 452 (1985); Rademacher et al., Proc. Natl. Acad. Sci. USA 91, 6123 (1994); Matsumoto et al., 128, 621 (2000)).

International patent application WO 2007/117505 discloses a polypeptide containing at least one IgG Fc region, said polypeptide having a higher anti-inflammatory activity and a lower cytotoxic activity as compared to an unpurified antibody. In this application it was found that an IgG preparation enriched for increased sialylation of the N-linked glycosylation site on the Fc fragment showed an enhanced anti-inflammatory activity in vivo. In contrast, it was concluded that Fab fragments displayed no anti-inflammatory activity in this in vivo assay.

The international application WO 2008/057634 by the same inventors as WO 2007/117505 discloses a polypeptide containing at least one IgG Fc region, wherein said at least one IgG Fc region is glycosylated with at least one galactose moiety connected to a respective terminal sialic acid moiety by a α-2,6 linkage. The polypeptide of WO 2008/057634 has a higher anti-inflammatory activity as compared to an unpurified antibody. Also in this application it was found that an IgG preparation enriched for increased sialylation of the N-linked glycosylation site on the Fc fragment showed an enhanced anti-inflammatory activity in vivo. In contrast, it was concluded that Fab fragments displayed no anti-inflammatory activity in this in vivo assay. Further evidence that the anti-inflammatory activity is due to increased sialylation on the Fc fragment, rather than Fab fragment, is provided in international application WO 2009/079382 by the same inventors.

In a commentary by Nimmerjahn & Ravetch (JEM 204, 11-15 (2007), the authors clearly teach that the sialylation in the Fc region is the key to the anti-inflammatory activity of IVIG. In addition they state that a generalized role for the antigen binding domain, located in the Fab regions, in the anti-inflammatory activity of IgG is unlikely, given that in their hands, intact IVIG and its Fc fragments have equivalent anti-inflammatory activity.

The international application WO 2007/005786 is directed to methods for controlling the properties of an Fc-containing molecule, said methods comprising altering the sialylation of the oligosaccharides in the Fc region. In this application it was found that the level of sialylation of the Fc oligosaccharides alters the affinity of recombinantly-produced therapeutic antibodies for Fcγ receptors, resulting in modulation of various aspects of the biological actions of these antibodies. It was further discovered that the removal of sialic acid from the Fc oligosaccharides enhances the avidity of recombinantly-produced therapeutic antibodies for their target molecule. However, the effect is believed to be entirely Fc mediated, as no differences in the intrinsic affinity between each Fab arm and the target were observed. The inventors of WO 2007/005786 hypothesize that the removal of the charged static group from the Fc oligosaccharide allows for more flexibility in the overall antibody structure, thus providing a higher potential of interaction for the two binding domains in relationship of one to the other.

A recent review article by Jefferis (Jefferis, R.; Nat Rev Drug Discov. 2009 March; 8(3):226-34) discusses glycosylation as a strategy to improve antibody-based therapeutics. According to Jefferis 2009, approx. 30% of polyclonal human IgG molecules bear N-linked oligosaccharides in the IgG Fab region and a higher level of galactosylation and sialylation for IgG Fab than for IgG Fc is observed. When present, the glycosylation is attached to the variable regions, and the functional significance of IgG Fab glycosylation of polyclonal IgG is not clear. Based on studies on monoclonal antibodies it is speculated that the glycosylation in the Fab region of an antibody can have a neutral, positive or negative influence on antigen binding. No incentive is given to study this further, nor to enrich the antibody population that is glycosylated in the Fab region.

Thus, antibody preparations having an increased amount of sialylation in the Fc region of antibodies have been intensely studied for the prevention and treatment of various diseases and also a potential role of glycosylation of the Fab region of antibodies has been discussed. However, whereas a number of antibodies are currently in use, there is still a need to provide alternative and/or improved antibody preparations having a more beneficial effectiveness in clinical applications.

The solution to this technical problem is achieved by providing the embodiments characterised in the claims. The inventors have surprisingly shown that enrichment of antibodies that show altered sialylation in the Fab region have altered immunomodulatory properties.

SUMMARY OF THE INVENTION

One embodiment of the invention is therefore a population of antibodies obtainable by enrichment from an antibody preparation, wherein the enriched population of antibodies has an altered amount of sialylation in the Fab region of the antibodies as compared to the antibody preparation prior to enrichment, and wherein the enrichment based on the altered sialylation in the Fab region has resulted in a population of antibodies with altered immunomodulatory properties of the enriched population when compared to the antibody preparation prior to enrichment.

Preferably the antibody population is produced by subjecting the antibody preparation to affinity chromatography on a *Sambucus nigra* agglutinin column or equivalent thereof, and (a) collecting the non-binding fraction (−SA fraction) and/or (b) eluting the binding fraction with acidic lactose (+SA fraction), whereby the −SA fraction has a reduced amount of sialylation in the Fab regions, and the +SA fraction has an increased amount of sialylation in the Fab regions, and whereby the fractions with altered amount of sialylation in the Fab regions have altered immunomodulatory properties.

A further preferred embodiment is the population of antibodies as described above, wherein the enriched population of antibodies has an altered amount of sialylation in the Fab region of the antibodies as compared to the antibody preparation prior to enrichment, wherein the amount of sialylation in the Fc portion is enriched by less than 100% (i.e. two-fold), preferably less than 50% (1.5 fold), more preferably by less than 30%, even more preferably by less than 20%, when measuring % sialylated glycopeptides of the total detected glycopeptides.

A further preferred embodiment is a population of antibodies as described above, wherein the enriched population of antibodies has an altered amount of sialylation in the Fab region of the antibodies as compared to the antibody preparation prior to enrichment, wherein the amount of sialylation in the Fab portion is altered by at least 1.25 fold, more preferably at least 1.5 fold, more preferably at least two fold, even more preferably at least three fold, most preferably at least four fold as compared to the amount of sialylation in the Fab region in the antibody preparation prior to enrichment.

Another embodiment of the invention is a method of enriching a population of antibodies from an antibody preparation, wherein the enriched population of antibodies has an altered amount of sialylation in the Fab region of the antibodies as compared to the antibody preparation prior to enrichment, the method comprising the steps of:
  (a) subjecting an antibody preparation to an affinity chromatography with an affinity for sialylated Fab regions of antibodies;
  (b-i) collecting the antibody population not bound in step (a); wherein said antibody population has a lower amount of sialic acid in the Fab region of the antibodies as compared to the antibody preparation prior to enrichment (−SA fraction); and/or
  (b-ii) eluting and collecting the antibody population bound in step (a), wherein said antibody population (+SA fraction) has a higher amount of sialic acid in the Fab region of the antibodies as compared to the antibody preparation prior to enrichment,
wherein the enrichment based on the altered amount of sialylation in the Fab region has resulted in a population of antibodies with altered immunomodulatory properties when compared to the antibody preparation prior to enrichment.

Preferably, the affinity chromatography in step (a) is with *Sambucus nigra* agglutinin. Preferably, the sialylation in the Fc portion of the resulting −SA fraction or the resulting +SA fraction differs from the Fc sialylation in the antibody preparation prior to affinity chromatography by less than 100% (2 fold), preferably by less than 50%, more preferably by less than 30%, most preferably by less than 20%, when measuring % sialylated glycopeptides of the total glycopeptides.

Preferably, the antibody preparation is a blood plasma immunoglobulin preparation, more preferably, a blood plasma immunoglobulin G preparation, even more a human blood plasma immunoglobulin G preparation, most preferably intravenous immunoglobulin G (IVIG) or subcutaneous immunoglobulin G (SCIG).

In a preferred embodiment, the amount of sialylation of the Fab region of the antibodies is further modified, preferably enzymatically. Preferably, the amount of sialylation in the −SA fraction is further reduced by enzymes which remove sialic acid residues, whereas the amount of sialylation in the +SA fraction is further increased by enzymes which add sialic acid residues.

One preferred embodiment is a population of antibodies or a method which results in a population of antibodies, wherein the altered amount of sialylation is a reduction in the amount of sialylation in the Fab region.

A second, alternative preferred embodiment of the invention is a population of antibodies or a method, wherein the altered amount of sialylation is an increase in the amount of sialylation in the Fab region.

A further embodiment of the invention is a pharmaceutical composition comprising the population of antibodies of the invention. Optionally the pharmaceutical composition may comprise a pharmaceutically acceptable carrier, excipient and/or diluent.

A further embodiment of the invention is a population of antibodies with altered sialylation in the Fab region as described above for use in medicine.

In a preferred embodiment, the population of antibodies of the invention is for use in the prevention and/or treatment of atherosclerosis, cancer and infections such as bacterial, viral or fungal infections.

In another preferred embodiment the population of antibodies of the invention is for use in the prevention or treatment of an inflammatory condition. Preferably, the inflammatory condition is an autoimmune disease or a neurodegenerative disease, for example, the autoimmune or neurodegenerative disease is Rheumatoid arthritis, Systemic Lupus Erythematosus (SLE), Antiphospholipid syndrome, immune thrombocytopenia (ITP), Kawasaki disease, Guillain Barré syndrome (GBS), multiple sclerosis (MS), chronic inflammatory demyelinating polyneuropathy (CIDP), skin blistering diseases, Dermatomyositis, Polymyositis, Alzheimer's Disease, Parkinson's Disease, Alzheimer's Disease related to Downs Syndrome, cerebral amyloid angiopathy, Dementia with Lewy bodies, Fronto-temporal lobar degeneration or vascular dementia. Preferably the population of antibodies used in the treatment of inflammatory conditions has an increased sialic acid content in the Fab regions.

DETAILED DESCRIPTION OF THE INVENTION

The present invention relates to a population of antibodies enriched from an antibody preparation, wherein the enriched population of antibodies has an altered amount of sialylation in the Fab region of the antibodies as compared to the antibody preparation prior to enrichment. Preferably, the population of antibodies is obtainable by enrichment from an antibody preparation, wherein the enriched population of antibodies has an altered amount of sialylation in the Fab region of the antibodies as compared to the antibody preparation prior to enrichment, and wherein the enrichment based on the altered sialylation in the Fab region has resulted in a population of antibodies with altered immunomodulatory properties of the enriched population when compared to the antibody preparation prior to enrichment.

The population of antibodies according to this embodiment is also referred to throughout the description as the "enriched population of antibodies of the present invention".

The term "population of antibodies" in accordance with all embodiments of the present invention refers to a group of antibodies that is either homogeneous, i.e. comprises several molecules of only one specific antibody or is heterogeneous, i.e. comprises a plurality of different antibodies. In either case, the population of antibodies preferentially consists of or comprises antibodies of the IgG class (see also below). However, it could also comprise or consist of antibodies of the IgM or IgA class or mixtures of immunoglobulins of IgG, IgM and/or IgA class.

In accordance with the present invention, the term "enriched population of antibodies" refers to a population of antibodies that is more concentrated in the sense that it comprises more antibodies having a certain feature of interest, i.e. an altered amount of sialylation in the Fab region of the antibodies, as compared to the antibody preparation prior to enrichment. The terms "amount of sialylation" and "amount of sialic acid" are used interchangeably herein. As defined below, the altered amount of sialylation may be either an increase or a decrease in the amount of sialylation in the Fab region of the antibodies. Thus, the enriched population of antibodies may for example be enriched for antibodies having a sialylation in their Fab region, therefore resulting in a population having an increased amount of sialylation as compared to the antibody population prior to enrichment. As another example, the enriched population of antibodies may also be enriched for antibodies devoid of sialylation in their Fab region, therefore resulting in a population having a decreased amount of sialylation as compared to the antibody population prior to enrichment. Preferably, the enriched population of antibodies differs from the antibody preparation prior to enrichment by having an amount of sialylation that is at least 1.25 times higher or lower, more preferably at least 1.5 times higher or lower, more preferably at least two times higher or lower such as at least three times or at least four times higher or lower as compared to the amount of sialylation in the Fab region in the antibody preparation prior to enrichment. More preferably, the amount of sialylation is at least five times higher or lower as compared to the amount of sialylation in the Fab region in the antibody preparation prior to enrichment. The term "times higher or lower" refers to a relative increase or decrease compared to the starting material when measuring % sialylated glycans of the total glycans. For example, if the antibody population prior to enrichment has an amount of sialic acid of 15% of the glycans, then an enriched population of antibodies having a three times higher or lower amount of sialic acid will have 45% or 5% glycans with sialic acid, respectively. In the case of IgG, the sialylation of Fc fragments is determined by digestion with a protease such as trypsin, followed by analysis of the resulting Fc-specific glycopeptides (for example as described in Example 2, method (a)), and the numbers for enrichment quoted herein refer to the fold enrichment or percentage of Fc-specific glycopeptides having one or more sialic acid residues, of the total Fc-specific glycopeptides. The total sialylation of an IgG molecule (including Fab and Fc sialylation) can be determined by digesting the tryptic peptides with N-Glycosidase F, followed by analysis of the released glycans (for example as described in Example 2, method (b)). In this case, the numbers refer to the number or percentage of glycans having one or more sialic acid residues of the total glycans.

The enriched population of antibodies may be an isolated and/or purified population of antibodies, depending on the choice of antibody preparation as a starting material used for enrichment and depending on the method of enrichment selected. A "purified population of antibodies" as used herein refers to a population of antibodies comprising only one class of antibody, such as IgGs. The population of antibodies may also be purified to the effect that it contains or essentially contains (i.e. to more than 90%) only antibodies of a specific subclass such as IgG1, IgG2, IgG3 or IgG4 or that it contains or essentially contains only antibodies of a defined specificity for an antigen. The term "isolated population of antibodies" as used herein refers to a population of antibodies that does not comprise any molecules other than the antibodies.

The term "antibody" as used throughout the present invention encompasses, for example, polyclonal or monoclonal antibodies. The term "antibody" also comprises derivatives or fragments thereof which still retain antigen binding specificity. Thus, also included are embodiments such as chimeric (human constant domain, non-human variable domain), single chain and humanized (human antibody with the exception of non-human CDRs) antibodies, as well as antibody fragments, like, inter alia, Fab or Fab' fragments. Antibody fragments or derivatives further comprise Fd, F(ab')$_2$, Fv or scFv fragments; see, for example, Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999.

The term "Fab region", as used throughout the present invention, refers to the region of an antibody composed of one constant and one variable domain from each heavy and light chain of the antibody, and which contains the sites involved in antigen binding. Each intact natural IgG antibody comprises two Fab regions. In accordance with the present invention, the term "Fab fragment" is used for those fragments of antibodies that are generally obtained when antibodies are digested with papain. Papain digestion results in the cleavage of the antibody above the disulfid bridges linking the two heavy chains and, thus, the release of the two individual Fab fragments. Digestion with pepsin, on the other hand, results in the release of the two Fab fragments linked together by the hinge region of the antibody, the so-called "F(ab')$_2$ fragment". With respect to antibodies not digested by these enzymatical digestions, the term "Fab region" refers to those parts of the antibody that would form the Fab and/or F(ab')$_2$ fragments if digestion with papain or pepsin was carried out. With respect to antibody fragments obtained by papain or pepsin digestion, the Fab region corresponds to the Fab fragment. In the case of a Fab fragment, the corresponding molecule is identical to a Fab region.

However, as the glycosylation in the Fab regions is located in the variable regions of the antibodies, in the context of the present invention, Fv regions, single chain Fv fragments or other fragments containing the variable regions of the antibodies are considered equivalents.

In accordance with all embodiments of the present invention, antibodies can be extracted from blood plasma or can be produced by any one of the various procedures known in the art, e.g. as described in Harlow and Lane (1988) and (1999), loc. cit. Thus, the antibodies may, for example, be synthetically produced, and may also include peptidomimetics. Further, techniques described for the production of single chain antibodies (see, inter alia, U.S. Pat. No. 4,946,778) can be applied. Also, transgenic animals or plants (see, e.g., U.S. Pat. No. 6,080,560) may be used to express (humanized) antibodies. For the preparation of monoclonal antibodies, any technique which provides antibodies produced by continuous cell line cultures can be used. Examples for such techniques known in the art, e.g. as described in Harlow and Lane (1988) and (1999), loc. cit. and include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al, Monoclonal Antibodies and Cancer Therapy, Alan R. Liss, Inc. (1985), 77-96). It is also envisaged in the context of this invention that the term "antibody" comprises antibody constructs which may be expressed in cells, e.g. antibody constructs which may be transfected and/or transduced via, amongst others, viruses or plasmid vectors.

The term "altered amount of sialylation" as used in accordance with the present invention refers to a change in the amount of sialic acid in a population of antibodies, wherein the sialic acids are located in the Fab region of the antibodies of said population. Thus, the amount of sialylation of the enriched population of antibodies is altered if the overall amount of sialic acid in the Fab region of the antibodies of the enriched population of antibodies differs from the overall amount of sialic acid in the Fab region of the antibodies of the antibody preparation prior to enrichment. The change in the amount of sialic acid might be an increased amount of sialic acid or a decreased amount of sialic acid. Determination of whether a population of antibodies has an altered amount of sialylation in the Fab region of the antibodies as compared to the antibody preparation prior to enrichment can be carried out using any of a variety of methods known in the art. For example, the amount of sialylation can be determined for both the antibody preparation prior to enrichment and the population of antibodies of interest and the results thus obtained can directly be compared. Methods for determining the amount of sialylation are well known in the art. Non-limiting examples include the methods as detailed in the example section or pepsin digestion of the antibodies of interest, followed by separation of the resulting F(ab')$_2$ and the pepsin fragments from the Fc fragment (for example using centricon) and quantification of the sialic acid in these fractions (for example with HPLC or MS or an enzyme based photometric assay, available from QA-bio LLC, Palm Desert, Calif.: qa-bio.com) as described, for example, in Current Protocols in Protein Science: Unit 12.4 (Hudson et al), 12.6 (Royle et al) and 12.7 (Harvey et al), John Wiley and Sons (2006). These methods can be used for the determination of altered amounts of sialylation of all the embodiments described herein. The amount of increase or decrease in sialylation is generally expressed as % sialylated glycans of the total glycans, or for Fc sialylation % sialylated glycopeptides of total glycopeptides.

In accordance with the present invention, the term "sialic acid" refers to N- or O-substituted derivatives of neuraminic acid, a monosaccharide with a nine-carbon backbone. The most common member of this family of neuraminic acid derivatives is N-acetylneuraminic acid (Neu5Ac or NANA). A further member of the family is N-glycolylneuraminic acid (NGNA or Neu5Gc), in which the N-acetyl group of Neu5Ac is hydroxylated. Also encompassed by the term sialic acid is 2-keto-3-deoxynonulosonicacid (KDN) (Nadano et al. (1986) J. Biol. Chem. 261: 11550-11557; Kanamori et al., J. Biol. Chem. 265: 21811-21819 (1990)) as well as 9-substituted sialic acids such as a 9-O—C—C6 acyl Neu5Ac like 9-O-lactyl-Neu5Ac or 9-O-acetyl-Neu5Ac, 9-deoxy-9-fluoro-Neu5Ac and 9 azido-9-deoxy-Neu5Ac (Varki, Glycobiology 2: 25-40 (1992); Sialic Acids: Chemistry, Metabolism and Function, R. Schauer, Ed. (Springer Verlag, New York (1992)).

In accordance with the present invention, the term "immunomodulatory properties" refers to the effect the population of antibodies exerts on the immune system. An immunomodulatory effect can be immunosuppression or immunostimulation. A variety of in vitro or in vivo methods are available to the skilled person to measure the immunomodulatory properties of a substance like a population of antibodies. For example, a monocyte-derived cell line, e.g. U937 cells, can be grown and differentiated with retinoic acid or vitamin D. They can then be stimulated, e.g. with interferon-γ or phytohemagglutinin, in the presence and absence of the test substances. After appropriate incubation, the amount of inflammatory markers such as IL-8 can be measured in the supernatants of the cells, and cell surface markers on the U937 cells, e.g. CD54, CD14 or CD45, can be determined, e.g. by fluorescence activated cell analysis (FACS analysis). Substances with immunosuppressive, e.g. anti-inflammatory, properties will result in a lower amount of inflammatory markers as compared to the control samples. Substances can also be ranked for their anti-inflammatory effects with such an assay; the lower the amount of inflammatory markers produced, the higher the anti-inflammatory effect. Another example is a method using peripheral blood mononuclear cells (PBMCs) isolated from human blood, stimulated with certain substances such as loxoribine or CpG in the absence or presence of test substances. The inhibition of interferon-α production by test substances will be an indicator of an immunosuppressive, e.g. anti-inflammatory effect. Similar assays, measuring immunostimulation, are also available. For example, the same methods as described above can be used, but without using stimulation by e.g. interferon or phytohemagglutinin or similar stimulants.

In accordance with the present invention it was surprisingly found that separating an antibody preparation using lectin affinity chromatography at a neutral or basic pH resulted in antibody populations that showed only small differences in the amount of sialylation in the Fc region of the antibodies but showed high differences in the amount of sialylation in the Fab region of the antibodies. As shown in example 4, these populations have different antigen recognition patterns which leads to beneficial effects using these fractions in clinical applications, such as for example in atherosclerosis, where a protective effect was shown in particular for the population having a reduced amount of sialic acid in the Fab region of the antibodies.

The present invention also relates to a method of enriching a population of antibodies from an antibody preparation, wherein the enriched population of antibodies has an altered amount of sialylation in the Fab region of the antibodies as compared to the antibody preparation prior to enrichment, the method comprising the steps of: (a) subjecting an antibody preparation to an affinity chromatography with an affinity for sialylated Fab regions of antibodies; (b-i) collecting the antibody population not bound in step (a); wherein said antibody population has a lower amount of sialic acid in the Fab region of the antibodies as compared to the antibody preparation prior to enrichment (−SA fraction), and/or (b-ii) eluting and collecting the antibody population bound in step (a), wherein said antibody population has a higher amount of sialic acid in the Fab region of the antibodies as compared to the antibody preparation prior to enrichment (+SA fraction), wherein the enrichment based on the altered amount of sialylation in the Fab region has resulted in a population of antibodies with altered immunomodulatory properties when compared to the antibody preparation prior to enrichment. Preferably, the affinity chromatography in step (a) is with *Sambucus nigra* agglutinin. In a preferred embodiment, the sialylation in the Fc portion of the −SA fraction or the +SA fraction differs from the Fc sialylation in the antibody preparation by less than 100% (2-fold), preferably less than 50%, more preferably less than 30%, most preferably less than 20%, when measuring % sialylated glycopeptides of the total glycopeptides.

The term "affinity chromatography with an affinity for sialylated Fab regions of antibodies" in accordance with the present invention relates to a chromatographic method of separating mixtures of antibodies, based on a specific interaction between the affinity matrix and the sialic acids present in the Fab region of antibodies. Several methods of separating antibodies based on their sialic acids are known to the skilled person, such as for example lectin chromatography, sialic acid specific chemical ligands, ion exchange chromatography (such as for example AIEX), hydrophobic or hydrophilic interaction chromatography or mixed mode liquid chromatography (e.g. anion-cation exchange/hydrophylic interaction chromatography) (Mant C T, J Sep Sci. 31, 2754, 2008). These methods may be adapted to allow for the separation of antibodies based on their sialic acids present in the Fab region, for example as detailed below and as shown in the examples of the present invention.

Because antibodies having low levels of sialylation or no sialylation in the Fab region will not be bound by the affinity chromatography in accordance with the present invention, the antibody population not bound in step (a) and collected in step (b-i) is an enriched population having a decreased amount of sialylation in the Fab region of the antibodies as compared to the preparation before the enrichment. In other words, this antibody population is a sialic acid depleted population. The antibody population bound in step (a) and collected in step (b-ii) is an enriched population having an increased amount of sialylation in the Fab region of the antibodies as compared to the preparation before the enrichment, due to the binding of antibodies having high levels of sialylation in the Fab region to the affinity chromatography. Thus, the antibodies of the starting population of antibodies is separated into enriched populations having either an increased or decreased amount of sialylation in the Fab region of the antibodies.

In a preferred embodiment of the method of the invention, at least one wash step is carried out between the steps (b-i) and (b-ii). Suitable washing solutions are well known to the skilled person and are selected from, for example, tris-buffered saline (TBS) or phosphate buffered saline (PBS).

In a preferred embodiment of the enriched population of antibodies of the invention or the method of the invention, the antibody preparation is a blood plasma immunoglobulin G preparation.

The term "blood plasma immunoglobulin G preparation" in accordance with the present invention refers to an immunoglobulin G preparation isolated from blood plasma. The immunoglobulin G to be isolated from blood plasma may have been secreted by circulating B-cells (antibody secreting plasma cells). The blood plasma immunoglobulin G preparation can be obtained from a mammal such as for example human, but also by way of non-limiting example from transgenic animals expressing a human immunoglobulin G repertoire, such as for example pig, goat, sheep or cow (reviewed in Echelard Y and Meade H., "Toward a new cash cow." Nat Biotechnol. 2002 September; 20(9):881-2).

In a more preferred embodiment, the blood plasma immunoglobulin G preparation is intravenous immunoglobulin G (IVIG).

"Intravenous immunoglobulin G (IVIG)", in accordance with the present invention, is well known to the skilled person and refers to a blood plasma preparation that contains the pooled IgG immunoglobulins extracted from the plasma of over one thousand blood donors. IVIG is used in medicine as an intravenously administered product for the treatment of diseases such as immune deficiencies, inflammatory and autoimmune diseases as well as acute infections. A preferred example of an IVIG is Privigen™.

In another more preferred embodiment, the blood plasma immunoglobulin G preparation is subcutaneous immunoglobulin G (SCIG).

"Subcutaneous immunoglobulin G (SCIG)" in accordance with the present invention, is well known to the skilled person and refers to a blood plasma preparation similar to IVIG, only that it is used in medicine as a subcutaneously administered product. A preferred example of a SCIG is Hizentra™.

In another more preferred embodiment, the blood plasma immunoglobulin G preparation is a human blood plasma immunoglobulin G preparation.

In another preferred embodiment of the method of the invention, the affinity chromatography with an affinity for sialylated Fab regions of antibodies is a lectin affinity chromatography at pH 8 to 11.

The term "lectin affinity chromatography" in accordance with the present invention relates to a chromatography wherein the affinity matrix is lectin. Lectins, such as agglutinins, are proteins which can bind specific carbohydrate molecules and are thus capable of separating proteins based on their glycan groups. Non-limiting examples of lectins suitable for use in the lectin affinity chromatography of the present invention are *Sambucus nigra* agglutinin (SNA, *Sambucus nigra*), wheat germ agglutinin (WGA, *Triticum vulgaris*) and *Maackia amurensis* lectin (MAL, *Maackia amurensis*) isoforms I and II (Mal I and Mal II).

In accordance with the present invention it was surprisingly found that adapting the pH employed in lectin affinity chromatography affects the binding abilities of lectin for sialic acid. Whereas lectins bind to sialic acid in Fc fragments at a neutral pH, almost no binding of Fc fragments to lectin was observed at a basic pH (as shown in example 3). Thus, when using a basic pH, a separation based on sialic acids in the Fab region of antibodies becomes possible, as shown in the examples.

In a more preferred embodiment, the pH value is between 9 and 10, more preferably the pH is 9.5.

In a preferred embodiment, the lectin is *Sambucus nigra* agglutinin. Affinity chromatography on this lectin may be performed at basic or neutral or even slightly acidic pH.

In another preferred embodiment of the method of the invention, the affinity chromatography with an affinity for sialylated Fab regions of antibodies is carried out using ligands specific for sialylation of the Fab region of antibodies.

"Ligands specific for sialylation of the Fab region of antibodies", in accordance with the present invention, are ligands that, firstly, specifically bind sialic acids and, secondly, specifically bind sialic acids in the Fab region but do not bind sialic acids contained in any other region of the antibodies. Such specific ligands may be obtained by methods well known to the skilled person, such as for example using receptor molecules which are synthetically produced according to principles of molecular recognition. The receptor molecules spot a target protein by recognising a protein with desired glycosylation pattern (e.g. sialylation) in a substance mixture, bind it simultaneously at various binding sites and enclose it physically in a tertiary structure. After that, the target protein is released again by changing the pH value or salt concentration of the elution buffer.

In a more preferred embodiment, the ligands specific for sialylation of the Fab region of antibodies are selected from synthetically produced ligands obtained for example by combinatory chemistry and ligand screening (Still W C, Acc. Chem. Res. 29, 155, 1996. Brady P, Chem. Soc. Rev. 26, 327, 1997. Patterson S, Tetrahedron Lett. 39, 3111, 1998).

In a more preferred embodiment of the method of the invention, the affinity chromatography has a lower affinity for sialylated Fc regions of antibodies than for sialylated Fab regions of antibodies, i.e. the affinity is selective for Fab sialylation over Fc sialylation. Thus, the affinity matrix employed in the method of the invention will preferentially bind sialic acids contained in the Fab region of the antibodies but not, or only to a smaller extent, bind sialic acids contained in the Fc region of the antibodies. Consequently, as the separation is based on Fab sialylation, the population of antibodies obtained in step (b-ii) is more enriched for antibodies having a Fab sialylation than for antibodies having a Fc sialylation and, similarly, the population of antibodies obtained in step (b-i) is more enriched for antibodies having no or almost no Fab sialylation irrespective of their Fc sialylation. Preferably, the Fc sialylation will differ by less than 100%, more preferably less than 50%, even more preferably less than 30%, most preferably less than 20%, when measuring % sialylated glycopeptides of the total glycopeptides.

The present invention further relates to a population of antibodies, wherein the population of antibodies has an altered amount of sialylation in the Fab region of the antibodies as compared to the antibody preparation prior to enrichment.

Determination of whether a population of antibodies has an altered amount of sialylation in the Fab region of the antibodies as compared to the antibody preparation prior to enrichment can be carried out as described above. An altered amount of sialylation is considered any amount of sialylation that is not identical to the amount of sialylation of IVIG within the limits of detection of the plethora of methods currently available. Preferably, the amount of sialylation of the population of antibodies is at least 1.25 times higher or lower, more preferably at least 1.5 times higher or lower, more preferably at least two times higher or lower such as at least three times or at least four times higher or lower as compared to the amount of sialylation in the Fab region in the antibodies in the antibody preparation prior to enrichment. More preferably, the amount of sialylation is at least five times higher or lower as compared to the amount of sialylation in the Fab region in the antibodies in the antibody preparation prior to enrichment. As described above, the term "times higher or lower" refers to a relative increase or decrease compared to the amount of sialic acid in the antibody preparation prior to enrichment.

In a preferred embodiment of the population of antibodies of the invention having an altered amount of sialylation in the Fab region of the antibodies as compared to the antibody preparation prior to enrichment, the population of antibodies is a blood plasma immunoglobulin G preparation.

In a more preferred embodiment, the blood plasma immunoglobulin G preparation is a human blood plasma immunoglobulin G preparation.

In preferred embodiment of the population of antibodies of the invention or the method of the invention, the amount of sialylation of the Fab region of the antibodies is further modified.

In this embodiment, the amount of sialylation is modified such that a further increase or decrease in sialylation in the Fab region of the antibodies is obtained, resulting in a further modification of the overall amount of sialylation of the respective population of antibodies. Both an increase as well as a decrease in the amount of sialic acid in the Fab region of the antibodies is envisaged. It is preferred that where a population of antibodies of the invention has an increased amount of sialic acid in the Fab region of the antibodies, the further modification is an additional increase in the amount of sialic acid in the Fab region of the antibodies. It is also preferred that where a population of antibodies of the invention has a decreased amount of sialic acid in the Fab region of the antibodies, the further modification is an additional decrease in the amount of sialic acid in the Fab region of the antibodies.

In this embodiment it is also envisaged that the pattern of sialylation, i.e. the type of sialic acid and/or their location in the Fab region of antibodies is further modified.

In a more preferred embodiment, the modification of the sialylation pattern is effected enzymatically.

The enzymatic modification may be carried out, for example, by using a sialyltransferase and a donor of sialic acid in order to increase the amount of sialic acid in the Fab region of the antibodies. Alternatively, a decrease in the amount of sialic acid in the Fab region of the antibodies may be achieved, for example, by using a sialidase enzyme, thereby removing sialic acids.

Non-limiting examples of sialyltransferases are ST3Gal III, also referred to as α-(2,3) sialyltransferase (EC 2.4.99.6), and α-(2,6) sialyltransferase (EC 2.4.99.1). α-(2,3) sialyltransferase catalyzes the transfer of sialic acid to the Gal of a Gal-β-1,3GlcNAc or Gal-β-1,4 GlcNAc glycoside (Wen et al., J. Biol. Chem. 267: 21011 (1992); Van den Eijnden et al., J. Biol. Chem. 256: 3159 (1991)) and is responsible for sialylation of asparagine-linked oligosaccharides in glycopeptides. Activity of α-(2,6) sialyltransferase results in 6-sialylated oligosaccharides, including 6-sialylated galactose. Different forms of α-(2,6) sialyltransferase exist and can be isolated from different tissues, or can be produced using recombinant techniques.

Non-limiting examples of sialidases (also referred to as neuraminidase, N-acetylneuraminate glycohydrolase) are sialidase Au, Alpha-(2-3,6,8,9) (EC 3.2.1.18); sialidase Cp, Alpha-(2-3,6) (EC3.5.1.18) and sialidase Sp Alpha-(2-3) (EC 3.5.1.18).

In order to achieve a selective modification of the amount of sialylation in the Fab region of the antibodies, the Fc region of an antibody may be protected from enzymatic activity by any of a variety of methods known in the art. For example, specific Fc-binding ligands might be employed to mask the Fc region. Non-limiting examples of such Fc-specific ligands include chemically synthesized ligands such as those described above or biological ligands such as soluble Fc receptors, Fc specific antibodies or protein A/G.

In addition, cell culture conditions may be altered to change the amount of sialylation of antibodies produced in cell culture. For example, an increased amount of sialic acid is obtained when the production rate is decreased and the osmolality is generally maintained in the range from about 250 mOsm to about 450 mOsm. This and other suitable cell culture conditions are described in, e.g., U.S. Pat. No. 6,656,466. Furthermore, it has been reported by Patel et al., (Patel et al., *Biochem J*, 285, 839-845 (1992)), that the content of sialic acid in antibody linked sugar side chains differs significantly if antibodies were produced as ascites or in serum-free or serum containing culture media. Moreover, it has also been shown that the use of different bioreactors for cell growth and the amount of dissolved oxygen in the medium influences the amount of galactose and sialic acid in antibody linked sugar moieties (Kunkel et al., *Biotechnol. Prog.*, 1.6, 462-470 (2000)).

In another preferred embodiment of the population of antibodies of the invention or the method of the invention, the altered amount of sialylation is a reduction in the amount of sialylation in the Fab region, as described above.

In another preferred embodiment of the population of antibodies of the invention or of the method of the invention, the altered amount of sialylation is an increase in the amount of sialylation in the Fab region, as described above.

The present invention further relates to the population of antibodies of the invention for use in medicine.

The present invention further relates to the population of antibodies of the invention for use in the treatment of inflammatory conditions, for example autoimmune diseases and/or neurodegenerative diseases, such as Rheumatoid arthritis, Systemic Lupus Erythematosus (SLE), Antiphospholipid syndrome, immune thrombocytopenia (ITP), Kawasaki disease, Guillain Barré syndrome (GBS), multiple sclerosis (MS), chronic inflammatory demyelinating polyneuropathy (CIDP), skin blistering diseases, Dermatomyositis, Polymyositis, Alzheimer's Disease, Parkinson's Disease, Alzheimer's Disease related to Downs Syndrome, cerebral amyloid angiopathy, Dementia with Lewy bodies, Fronto-temporal lobar degeneration or vascular dementia. Preferably, the population of antibodies for use in these conditions has an increased sialic acid content in the Fab regions.

As shown in example 6, the populations of antibodies having an altered amount of sialylation in the Fab region of the antibodies may, for example, be used in the treatment of diseases such atherosclerosis.

The present invention also relates to a composition comprising the population of antibodies of the invention.

The term "composition" in accordance with the present invention relates to a composition which comprises at least an enriched population of antibodies from an antibody preparation, wherein the enriched population of antibodies has an altered sialylation pattern in the Fab region of the antibodies as compared to the antibody preparation prior to enrichment or which comprises at least a population of antibodies, wherein the population of antibodies has an altered sialylation pattern in the Fab region of the antibodies as compared to the antibody preparation prior to enrichment. The composition may, optionally, comprise further molecules capable of altering the characteristics of the population of antibodies of the invention thereby, for example, reducing, stabilizing, delaying, modulating and/or activating the function of the antibodies. The composition may be in solid, or liquid form and may be, inter alia, in the form of (a) powder(s), (a) tablet(s), (a) solution(s) or (an) aerosol(s).

In a preferred embodiment, the composition of the invention is a pharmaceutical composition optionally further comprising a pharmaceutically acceptable carrier, excipient and/or diluent.

In accordance with the present invention, the term "pharmaceutical composition" relates to a composition for administration to a patient, preferably a human patient. The pharmaceutical composition of the invention comprises the populations of antibodies, recited above. The pharmaceutical composition of the present invention may, optionally and additionally, comprise a pharmaceutically acceptable carrier. By "pharmaceutically acceptable carrier" is meant a non-toxic solid, semisolid or liquid filler, diluent, encapsulating material or formulation auxiliary of any type. Examples of suitable pharmaceutical carriers are well known in the art and include sodium chloride solutions, phosphate buffered sodium chloride solutions, water, emulsions, such as oil/water emulsions, various types of wetting agents, sterile solutions, organic solvents etc. Preferably the carrier is a parenteral carrier, more preferably a solution that is isotonic with the blood of the recipient. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or further immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

Compositions comprising such carriers can be formulated by well known conventional methods. Generally, the formulations are prepared by contacting the components of the pharmaceutical composition uniformly and intimately with liquid carriers or finely divided solid carriers or both. Then, if necessary, the product is shaped into the desired formulation.

These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician. The pharmaceutical composition may be for administration once or for a regular administration over a prolonged period of time. Generally, the administration of the pharmaceutical composition should be in the range of for example 10 µg/kg of body weight to 2 g/kg of body weight for a single dose. However, a more preferred dosage might be in the range of 100 µg/kg to 1.5 g/kg of body weight, even more preferably 1 mg/kg to 1 g/kg of body weight and even more preferably 10 mg/kg to 500 mg/kg of body weight for a single dose. Administration of pharmaceutical compositions of the invention may be effected by different ways, e.g., by intravenous, intraperitoneal, subcutaneous, intramuscular, intradermal, oral, intranasal or intrabronchial administration.

The components of the pharmaceutical composition to be used for therapeutic administration must be sterile. Sterility is readily accomplished by filtration through sterile filtration membranes (e.g., 0.2 micron membranes).

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection. Preservatives and other additives may also be present such as, for example, antimicrobials, anti oxidants, chelating agents, and inert gases and the like. The pharmaceutical composition may comprise further agents depending on the intended use of the pharmaceutical composition.

The pharmaceutical composition may be particularly useful for the treatment of diseases, preferably diseases as disclosed below.

The present invention also relates to the population of antibodies of the invention for use in the prevention and/or treatment of atherosclerosis, cancer and infections such as bacterial, viral or fungal infections.

In accordance with the present invention, "atherosclerosis" refers to a chronic disease affecting arterial blood vessel. It is a chronic inflammatory response in the walls of arteries, in large part due to the accumulation of macrophage white blood cells and promoted by low density lipoproteins without adequate removal of fats and cholesterol from the macrophages by functional high density lipoproteins (HDL). It is caused by the formation of multiple plaques within the arteries. Inflammation is central at all stages of atherosclerosis and both innate and adaptive immuno-inflammatory mechanisms are involved. Disease progression is associated with formation of autoantibodies to oxidized lipoproteins and increase in circulating cytokines and inflammatory markers.

"Cancer", in accordance with the present invention, refers to a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system).

According to the present invention, an "infection" is the detrimental colonization of a host organism by a foreign species. In an infection, the infecting organism seeks to utilize the host's resources in order to multiply (usually at the expense of the host). The host's response to infection is inflammation.

Bacterial infections, in accordance with the present invention include but are not limited to Bacterial Meningitis, Cholera, Diphtheria, Listeriosis, Pertussis (Whooping Cough), Pneumococcal pneumonia, Salmonellosis, Tetanus, Typhus, Tuberculosis, *Staphylococcus aureus* or Urinary Tract Infections.

Viral infections, in accordance with the present invention include but are not limited to Mononucleosis, AIDS, Chickenpox, Common cold, Cytomegalovirus Infection, Dengue fever, Ebola Haemorrhagic fever, Hand-foot and mouth disease, Hepatitis, Influenza, Mumps, Poliomyelitis, Rabies, Smallpox, Viral encephalitis, Viral gastroenteritis, Viral encephalitis, Viral meningitis, Viral pneumonia or Yellow fever.

Fungal infections in accordance with the present invention include but are not limited to Aspergillosis, Blastomycosis, Candidiasis, Coccidioidomycosis, Cryptococcosis, Histoplasmosis or Tinea pedis.

It is particularly preferred that the population of antibodies of the invention may be used in the prevention and/or treatment of infections not amenable to traditional treatment regimens, for example due the occurrence of antibiotica resistance.

The present invention further relates to the population of antibodies of the invention for use in the treatment of inflammatory conditions, for example autoimmune diseases and/or neurodegenerative diseases, such as Rheumatoid arthritis, Systemic Lupus Erythematosus (SLE), Antiphospholipid syndrome, immune thrombocytopenia (ITP), Kawasaki disease, Guillain Barré syndrome (GBS), multiple sclerosis (MS), chronic inflammatory demyelinating polyneuropathy (CIDP), skin blistering diseases, Dermatomyositis, Polymyositis, Alzheimer's Disease, Parkinson's Disease, Alzheimer's Disease related to Downs Syndrome, cerebral amyloid angiopathy, Dementia with Lewy bodies, Fronto-temporal lobar degeneration or vascular dementia. Preferably, the population of antibodies for use in these conditions has an increased sialic acid content in the Fab regions.

The term "inflammatory condition" refers to abnormalities associated with inflammation, which underlie a large number of human diseases. Inflammation is a complex biological response to harmful stimuli, and is the body's attempt to remove the harmful stimulus and initiate healing. However, abnormalities can occur, leading to inflammatory conditions, such as chronic inflammation or autoimmune diseases.

The term "autoimmune disease" refers to conditions where the immune system attacks self-antigens. Examples include rheumatoid arthritis, multiple sclerosis, Lupus, myasthenia gravis, psoriasis.

The term "neurodegenerative disease" refers to conditions where a progressive loss of structure or function of neurons is observed, including death of neurons. Examples of neurodegenerative diseases include Alzheimer's disease, Parkinson's disease, multiple sclerosis, Huntington's disease.

All of the diseases described herein are well known to the skilled person and are defined in accordance with the prior art and the common general knowledge of the skilled person.

For use in the prevention and/or treatment of atherosclerosis it is particularly preferred that a population of antibodies having a decreased amount of sialic acid in the Fab region of the antibodies is used.

The figures show:

FIG. 1: Fractionation of IVIG using lectin affinity chromatography (SNA). A typical chromatogram is shown (A). Total sialic acid content in IgG was monitored with lectin blot using non-reducing conditions (B and C) or reducing conditions (D) during separation with SDS-PAGE. Shown is a Coomassie stained gel (B) and a SNA-biotin probed blot (C and D). Heavy and light chain sialylation could be detected (D).

Figure 2:
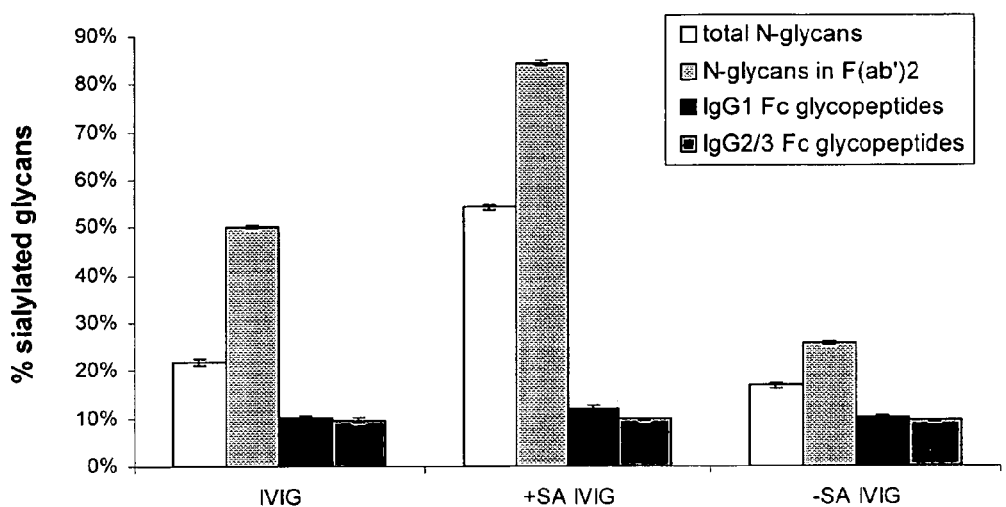

FIG. 2: Sialylated N-glycans in IVIG were measured by LC-MS analysis (as described in examples 2 and 4). Relative amounts of total N-glycans, Fc-specific glycopeptides and F(ab')$_2$-glycans were calculated for the different IVIG fractions. F(ab')$_2$-glycans were produced from IVIG, −SA IVIG and +SA IVIG by pepsin digestion.

Figure 3:
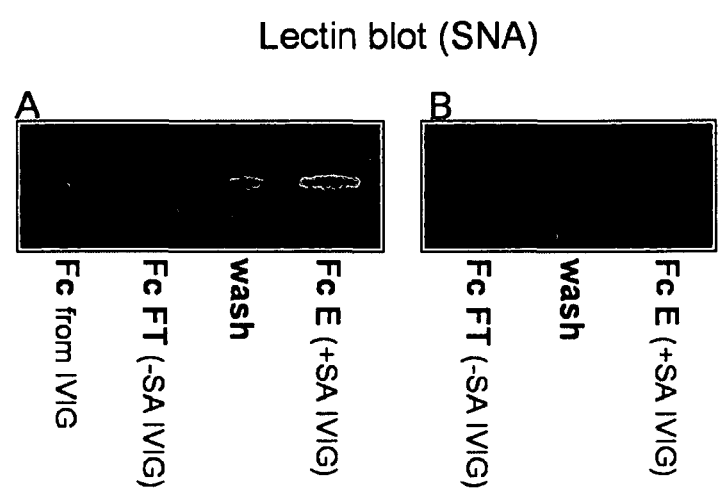

FIG. 3: Comparison of different lectin affinity chromatography conditions. Lectin blot analysis of Fc fragments from IVIG separated using lectin affinity chromatography at pH 7.5 (A) or pH 9.5 (B). Fc FT: flowthrough of loaded Fc (sialic acid depleted fraction; −SA Fc); FcE: Eluate (sialic enriched fraction; +SA Fc).

Figure 4:
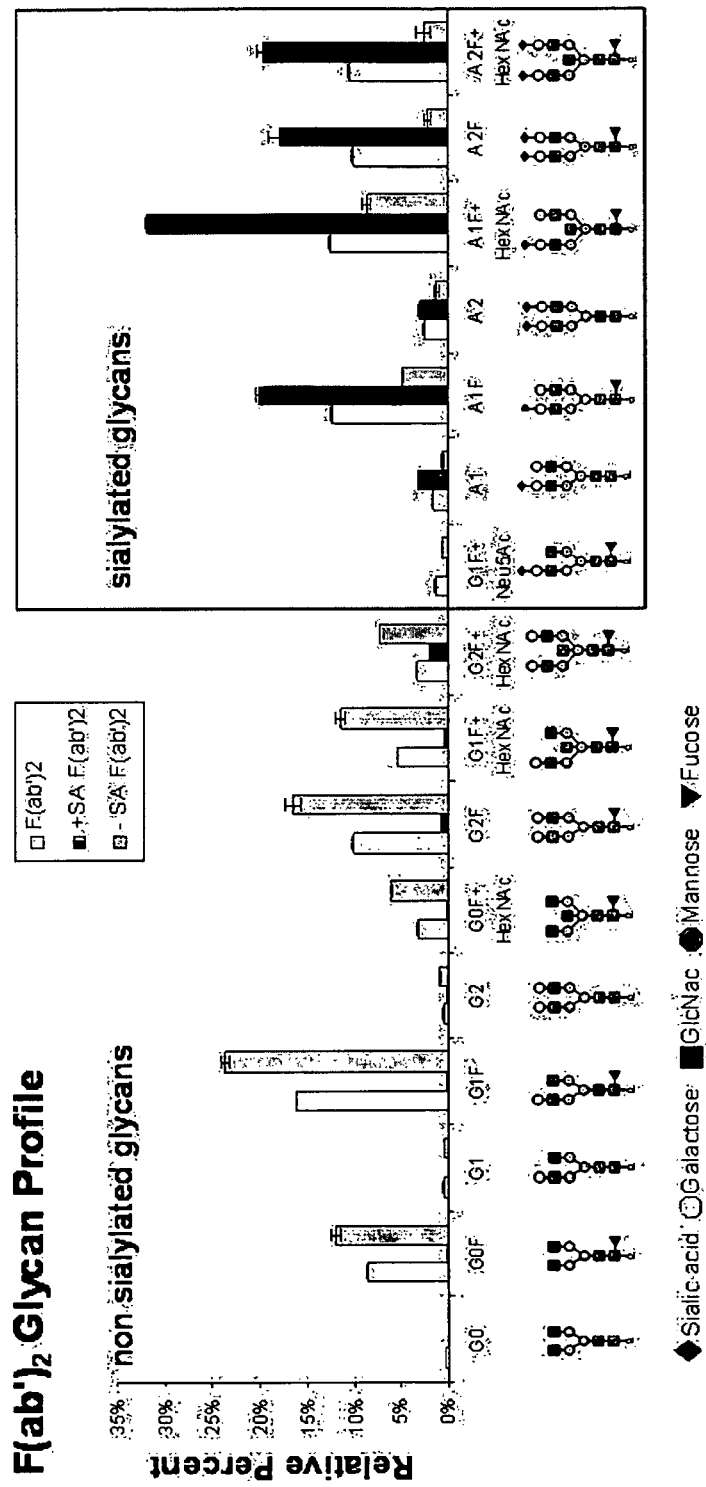

FIG. 4: Glycan profiles of source and fractioned F(ab')$_2$ fragments. F(ab')$_2$ fragments from IVIG were separated using lectin affinity chromatography. Glycans were released from F(ab')$_2$ by PNGaseF digestion, purified by C18 chromatography, converted to alditols and analysed with LC-MS in negative mode on an Agilent Q-TOF using a graphitized carbon HPLC column for glycan separation.

Figure 5:
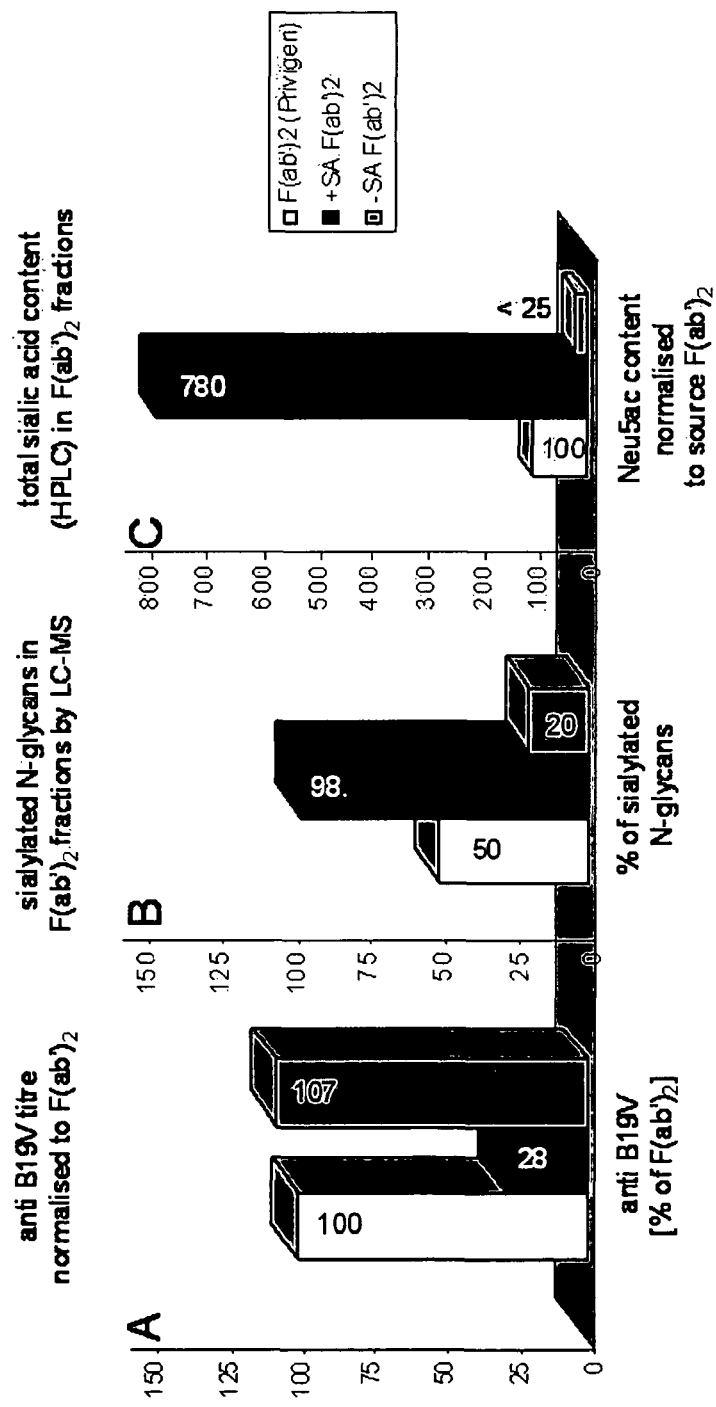

FIG. 5: Distribution of specific antibodies and sialic acid in F(ab')$_2$. The contribution of Fab sialylation in the lectin based separation was addressed by characterization of +/−SA fractions produced from F(ab')$_2$ fragments from IVIG. Relative anti-B19 virus titre per gram F(ab')$_2$ was measured using a commercial ELISA Kit and normalised to F(ab')$_2$ from IVIG (A). Relative amounts of sialylated N-glycans were calculated from LC-MS analysis of the F(ab')$_2$ fractions (B) and from quantifications of acid released sialic acid per IgG (Mol/Mol) with HPLC (C).

Figure 6:
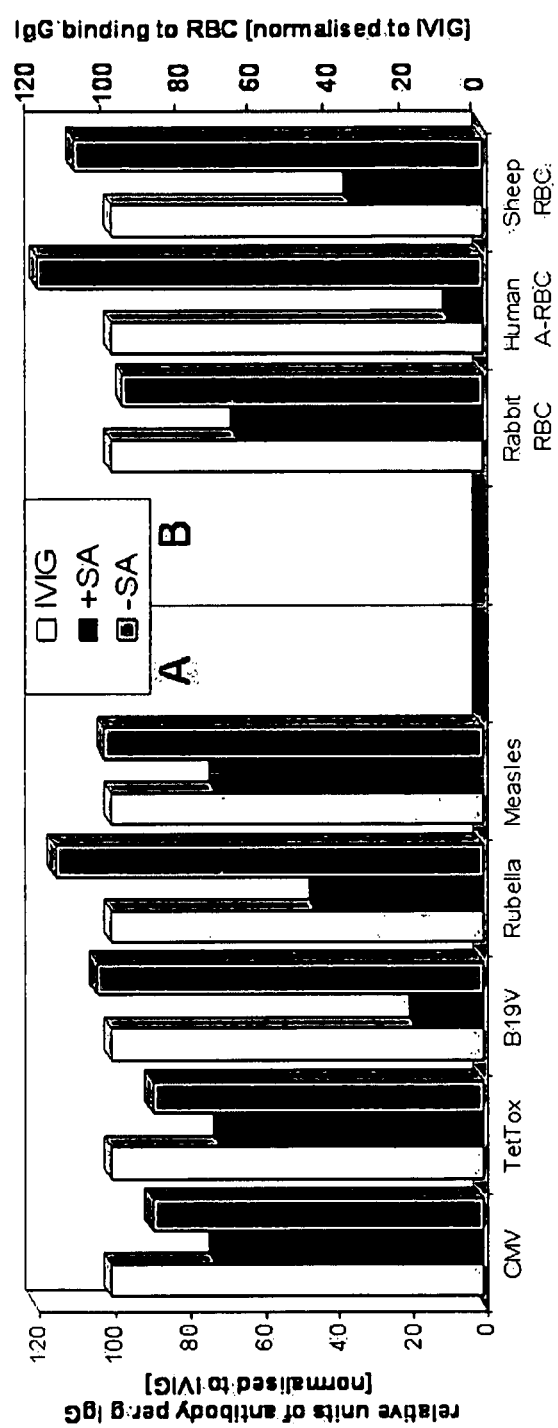

FIG. 6: Distribution of specific antibodies into sialic acid enriched vs. depleted fractions of IVIG. The distribution of specific antibodies for Cytomegalo virus (CMV), tetanus toxin (TetTox), B19 virus (B19V), Rubella and Measels was measured using commercial ELISA kits (Panel A). The binding to rabbit, sheep and human erythrocytes was measured by FACS analysis using fluorescence-labelled anti human IgG secondary antibodies.

Figure 7:
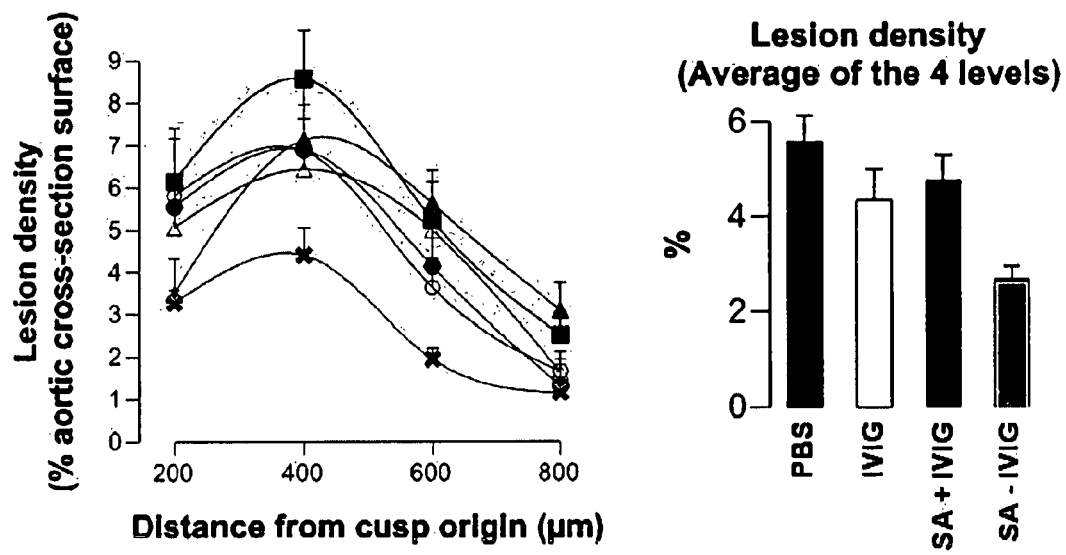

FIG. 7: Lesion density measured at 200, 400, 600 and 800 µm from the appearance of the aortic cusps in mice treated with total IVIG, 'IVIG+SA' or 'IVIG−SA' and control mice ('PBS'). Lesion density represents the percentage of the aortic cross-section area occupied by the lesions. Top left and right panels are equivalent but are averaged with the values of the 4 levels analyzed on the right panel. Tables below plots: Fischer posthoc test. S: statistically significant.

Figure 8:
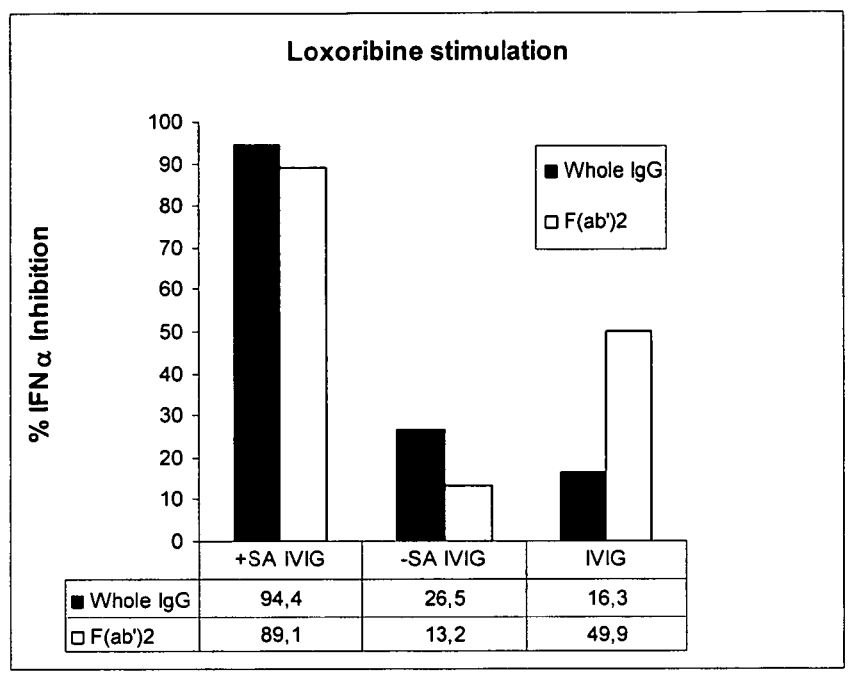

FIG. 8: Inhibition of interferon-alpha (IFN-α) production by peripheral blood mononuclear cells, stimulated with (a) TLR7 agonist Loxoribine (200 µM) by IVIG or the corresponding F(ab')2 fragment fractions, enriched for increased (+SA) or decrease (−SA) sialylation in the Fab region by affinity chromatography on *Sambucus nigra* agglutinin.

EXAMPLES

The following Examples are intended to illustrate but not to limit the invention.

Example 1

Fractionation of IVIG using 2,6 Sialic Acid Specific *Sambucus nigra* Agglutinin (SNA)

1 g IVIG in 100 ml tris-buffered saline (TBS), 0.1 mM CaCl$_2$ at pH 9-10 was recycled for 1 h on a 100 ml *Sambucus nigra* agglutinin (SNA) column. The flowthrough together with a 100 ml TBS/CaCl$_2$ wash was collected. After washing with 2×200 ml of TBS, the fraction bound to the SNA column (+SA IVIG) was eluted with 200 ml of 0.5M Lactose in 0.2M acetic acid. The flowthrough fraction was run a second time over the column to obtain −SA IVIG (FIG. 1).

Total sialic acid content in IgG was monitored with SDS PAGE (non-reducing conditions) and lectin blot (FIG. 1). The resulting IVIG fractions were separated with SDS PAGE using Nupage 10% BisTris Gels. The gels were stained with Coomassie and blotted on Nitrocellulose. The blots were probed with biotin-SNA and AP-streptavidin and visualised with chromogenic substrate. In FIG. 1D, heavy and light chains were separated with SDS PAGE under reducing conditions. In lectin blots probed with SNA-biotin, both chains are clearly visible indicating light chain sialylation. Hence, significant Fab sialylation could be detected in +SA IVIG.

Quantification of Sialic Acid

Sialic acid was released by acidic hydrolysis and derivatization was done with 1,2-diamino-4,5-methylenedioxybenzene dihydrochloride (DMB). Quantification was performed with Reverse Phase High Performance Liquid Chromatography (RP-HPLC) using N-acetyl neuraminic acid (Neu5Ac) as a standard and expressed as sialic acid per IgG (weight/weight or Mol/Mol).

With this method, a 5 fold increase of total sialic acid in +SA IVIG and a 2 fold decrease of total sialic acid in −SA IVIG per IgG (Mol/Mol) was observed as compared to IVIG before separation (data not shown).

Example 2

Glycan Analysis

To investigate the glycosylation profile of IVIG before and after separation, tryptic glycopeptides derived from the Fc region of a typical IVIG preparation were identified and profiled and the total N-glycan population of IVIG was profiled through glycan release and analysis.

Methods (a) Determination of IgG1 and IgG2/3 Fc Glycan Profile by Peptide Mapping.

IVIG samples were analyzed by liquid chromatography-mass spectrometry (LC-MS) after tryptic digestion to determine the glycan profile specific to the IgG1 and IgG2/3 Fc regions. The glycopeptide monitored for the IgG2 Fc region may also be found in the IgG3 Fc region, for this reason they are referred to as IgG2/3. Based on known relative abundance of IgG subclasses in serum, the majority of the signal seen for the IgG2/3 peptide is expected to originate from IgG2 molecules. Denaturation, reduction (heating with guanidinium-HCl and DTT) and alkylation (with Iodoacetamide) was followed by tryptic digestion using a 1:50 enzyme to substrate ratio. Tryptic peptides were isolated and purified on a C18 Solid Phase Extraction (SPE) spin column, and dried in tubes under vacuum. LC-MS analysis was performed on an Agilent Q-TOF system using an Agilent Proshell 300SB-C18 column for peptide separation. Chromatograms were extracted and integrated for each IgG1 and IgG2/3 glycopeptide, summing the [M+2H]2+ and [M+3H]3+ signals and using the calculated monoisotopic mass of the predicted structure. Data was analyzed and processed using Agilent MassHunter Software, version B.02.00 (Huddleston et al. Anal Chem 65, 877, 1993). Identification of IgG Glycopeptides.

LC-MS analysis of the tryptic digests resulted in complex chromatograms. In an effort to identify the potential glycopeptides, sequences of the heavy chain constant region for IgG subclasses 1 to 4 were obtained from the Entrez protein data base (accession numbers 12054072, 12054074, 12054076, and 12054078 respectively). Sequences were digested in silico. The peptides listed in Table 1 were identified as potential glycopeptides by the presence of an N-linked glycosylation consensus sequence. The theoretical weight of these peptides coupled to the common IgG glycan G0F, and the predicted [M+3H]3+ ions were also calculated.

$NH_4HCO_3$) and analyzed in duplicate by LC-MS in negative mode. Glycan separation was performed on a graphitized carbon high HPLC column using a 10 mM $NH_4HCO_3$/acetonitrile mobile phase system. Chromatograms were extracted and integrated for each glycan, summing the signals from the [M−1H]1−, [M−2H]2−, and [M−3H]3− signals of the glycan alditols. The preparation and analysis of the glycan alditols is similar to previously reported work (Karlsson et al. Rapid Commun Mass Spectrom 18, 2282, 2004).

Results

The sialylation level in Fc was not considerably higher in +SA IVIG compared to IVIG and −SA IVIG. As shown in FIG. 2, the % sialylated glycopeptides of total glycopeptides in the Fc regions changed only by less than 20%, i.e. from 10.3% to 12.1% of total glycopeptides). On the other hand, the sialylation level of the total N-glycans, including sialylation in Fab and Fc regions, is significantly higher in the +SA IVIG fraction (FIG. 2): it is increased by almost 70%, i.e. from 50.0% to 84.5% of total glycans. Based on these results it can be concluded, that the higher respectively lower sialylation level is mainly due to a different sialylation in the Fab region of IVIG.

In summary, the fractionation method described in Example 1 results in IgG preparations that are higher sialylated (+SA IVIG) or lower sialylated (−SA IVIG) compared to the source IgG preparation (IVIG). The observed higher sialylation level is mainly due to a higher sialic acid content in the Fab region of IgG.

TABLE 1

List of predicted glycopeptides from the four IgG subclasses. N-linked glycosylation consensus sequences are highlighted in bold. The calculated monoisotopic masses of the bare peptide, peptide connected to the G0F glycan, and the [M + 3H]3+ ion are given

| IgG Subclass | Predicted tryptic glycopeptides | SEQ ID NO | Monoisotopic mass of peptide (Da) | Mass with G0F glycan (Da) | [M + 3H]$^{3+}$ ion (m/z) |
|---|---|---|---|---|---|
| 1 | EEQYNSTYR | 1 | 1188.5047 | 2633.0386 | 878.6874 |
| 2 | EEQFNSTFC*VVSVLTVVHQDWLNGK | 2 | 2935.4016 | 4379.9354 | 1460.9863 |
| 3 | EEQYNSTFR | 3 | 1172.5098 | 2617.0437 | 873.3557 |
| 4 | EEQFNSTYR | 4 | 1172.5098 | 2617.0437 | 873.3557 |

*Samples were treated with iodoacetamide during sample preparation. The calculated mass for the cysteine-containing peptide includes the mass of one carboxyamidomethyl group to account for this treatment.

(b) Determination of Global Glycan Profile

Samples were analyzed as follows to determine the global glycan profile. Dried tryptic peptides derived from 250 μg of each sample were reconstituted in 50 μL 100 mM $NH_4HCO_3$ and incubated with 250 U N-Glycosidase F (PNGase F) at 37° C. overnight. A second C18 SPE purification was performed to separate the deglycosylated tryptic peptides from the released glycans. The released glycans were converted to alditols using a basic sodium borohydride solution, incubating overnight at 45° C. Following decomposition of remaining borohydride, the glycan alditols were desalted in a Dowex 50 WX4-400 ion exchange resin spin column and dried. Repeated addition and evaporation of 1% acetic acid in methanol was used to remove remaining boric acid. Glycan alditols were reconstituted in starting mobile phase (10 mM Example 3

Comparison of Lectin Affinity Chromatography at pH 7.5 or 9.5

To compare the effect of different pH conditions applied in lectin affinity chromatography on the binding affinities for sialylated Fc, IVIG was digested with papain (papay latex, 0.7 U/mg IgG for 2 hours at 37° C.). The Fc fragments were purified using protein A, size exclusion chromatography (SEC) and protein L (as described, for example, in Current protocols in Immunology: Unit 2.7 and 2.8 (Andrew et al) John Wiley and Sons (1997). The Fc fragments produced from IVIG were loaded onto SNA columns and separated using the method as described above, with the exception that TBS of either pH 7.5 or pH 9.5 was used. Equal aliquots of the resulting fractions were separated with SDS page (Nupage 10% BisTris Gels) and blotted on Nitrocellulose, the blots were probed with biotin-SNA and AP-streptavidin and visualised with chromogenic substrate (FIG. 3).

The lectin chromatography carried out at neutral pH (pH 7.5) resulted in a significant enrichment of sialylated Fc fragments (FIG. 3A, Eluate, E). On the other hand, using alkaline conditions (pH 9.5) resulted in barely detectable amounts of higher sialylated Fc as shown in FIG. 3B (Eluate, E). These findings are in line with the results of example 2, where no significant differences in Fc sialylation between the +SA fraction and the −SA fraction could be detected. As the use of alkaline pH conditions results in a very low binding affinity in lectin chromatography for sialylated Fc but nonetheless in an increased sialylation level of the total N-glycans, this indicates that this sialylation is in the Fab region.

Furthermore, this experiment shows, that when isolated Fc fragments are separated using lectin affinity chromatography, this leads to fractions with different Fc-sialylation levels compared to the separation of intact IgG molecules. This can be explained with the absence of the lectin binding Fab region.

Example 4

Glycan Analysis of F(ab')$_2$ and +/−SA F(ab')$_2$

F(ab')$_2$ were produced by pepsin digestion of IVIG. IVIG was digested with pepsin (0.5 mg/g IVIG) in acetate buffer pH 4.0 for 2 hours at 37° C. The reaction was stopped by adding 2M Tris base until a pH of 8 was reached. Concentration and purification from small digestion products and buffer exchange to PBS was performed using a Centricon (30'000 Mw cut-off) (as described, for example, in Current protocols in Immunology: Unit 2.7 and 2.8 (Andrew et al) John Wiley and Sons (1997)). Sialic acid enriched and depleted F(ab')$_2$ were produced by lectin affinity chromatography using SNA-agarose. F(ab')$_2$ (80 mg in 12 ml TBS, 0.1 mM CaCl$_2$, pH 9.5) was loaded for 1 hour on 12 ml of SNA-agarose. The flowthrough fraction was collected and termed −SA F(ab')$_2$. After washing with 2×24 ml of TBS, the +SA F(ab')$_2$ fraction was eluted with 24 ml of 0.5M lactose in 0.2M acetic acid.

Samples were analyzed by LC-MS after tryptic digestion. Denaturation, reduction, and alkylation of material was followed by tryptic digestion as described above. Samples were analyzed as described above (example 2) to determine the global glycan profile.

Profiling of Whole-IVIG Glycans and F(ab')2 Glycans

Relative quantitation of 16 distinct glycan species was performed for samples after glycan release and conversion to alditols. In general, the lectin-bound fraction shows a decrease in non-sialylated glycans and an increase in sialylated glycans in comparison to the unfractionated samples. Conversely, the unbound fraction was lower in sialylated glycans and higher in non-sialylated glycans than the unfractionated sample. Lectin-bound F(ab')$_2$ contains almost no non-sialylated glycans. (FIG. 4, FIGS. 5B and C)

Distribution of Specific Antibodies and Sialic Acid in F(ab')$_2$.

The contribution of Fab sialylation in the lectin based separation was addressed by characterization of +/−SA fractions produced from F(ab')$_2$ fragments form IVIG. In +SA F(ab')$_2$ a higher relative amount of sialylated N-glycans was observed with LC-MS analysis and a higher amount of total sialic acid was detected when quantifying acid released sialic acid with HPLC (FIGS. 5B and C). Differences in anti-B19 virus titres indicate that +SA vs. −SA F(ab')$_2$ fractions have a different antigen recognition pattern (FIG. 5A).

Example 5

Distribution of Specific Antibodies into Sialic Acid Enriched vs. Depleted Fractions of IVIG The distribution of specific antibodies for Cytomegalo virus (CMV), tetanus toxin (TetTox), B19 virus (B19V), Rubella and Measles was measured using commercial ELISA kits (FIG. 6A). The binding to rabbit, sheep and human erythrocytes was measured by FACS analysis using fluorescence-labelled and anti human IgG secondary antibodies.

The results show that different relative antibody titres are found in the 3 IVIG fractions for the measured antigens per gram IgG (FIG. 6). This difference in the antigen recognition pattern of the IVIG fractions may lead to enhanced effects using either the +SA IVIG or the −SA IVIG fraction in different clinical applications.

Example 6

In Vivo Comparison of the Atheromodulating Activities of Fractions of IVIG Enriched for Sialylation of Fab with Fractions of IVIG Depleted of Sialylation of Fab Atherosclerosis is a chronic disease of the arterial wall where both innate and adaptive immunoinflammatory mechanisms are involved. Inflammation is central at all stages of atherosclerosis. It is implicated in the formation of early fatty streaks, when the endothelium is activated and expresses chemokines and adhesion molecules leading to monocyte/lymphocyte recruitment and infiltration into the subendothelium. It also acts at the onset of adverse clinical vascular events, when activated cells within the plaque secrete matrix proteases that degrade extracellular matrix proteins and weaken the fibrous cap, leading to rupture and thrombus formation. Disease progression is associated with formation of autoantibodies to oxidized lipoproteins and increase in circulating cytokines and inflammatory markers.

Atherosclerosis and IVIG

Polyclonal immunoglobulin preparations (IVIG) inhibit atherosclerosis (Nicoletti, *Clin. Invest.* 102:910-918, 1998). The demonstration was performed in the Apolipoprotein E knockout (ApoE KO) mouse, a genetic model of cholesterol-induced atherosclerosis, in which both the innate and the adaptive immunity play a pivotal role. It was shown that injections of 7-week-old male apo E knockout mice with IVIG during a 5-day period reduced fatty streak formation over a 2-mo period on cholesterol diet by 35%. Fibrofatty lesions induced by diet treatment for 4 months were reduced by 50% in mice receiving IVIG after 2 months on the diet. While these results have been confirmed and reviewed by several groups, the precise mechanisms by which IVIG confers atheroprotection remain largely elusive.

Material and Methods

Three preparations of IVIG were used: total IVIG ('IVIG total'), sialic acid enriched IVIG fractions ('IVIG+SA') and sialic acid depleted IVIG fractions ('IVIG−SA') obtained as described above in example 1. These preparations were injected intraperitoneally at the dose of 10 mg/mouse/injection. Mice (6-7 week-old) received injections for 5 consecutive days. Saline was injected in control mice ('PBS'). In total, 10 mice per group of ApoE KO mice (n=10/group) were included. Mice were sacrificed 2 months after the first injection. No abnormal reaction of mice in response to any of the product injected was noticed.
Results Atherosclerosis development was assessed at the level of the aortic root. There was no statistical difference in the total surface area of the aorta indicating that IVIG injections did not induce major vascular remodeling. However, lesion size was significantly reduced in mice treated with IVIG preparations. Total IVIG and IVIG+SA conferred a similar protection with an average of 25% decrease the lesion density in these groups of mice. Mice that received the lower-sialylated IVIG (IVIG−SA) preparation were the most protected and developed lesions half the size that of the controls (FIG. 7).

Example 7

The Effect of Fab Sialylation on Anti-Inflammatory Activity Tested in an in Vitro Cell Stimulation Assay In various autoimmune and neurodegenerative diseases inflammatory conditions correlate with the disease. In an in vitro cell culture assay the inflammatory conditions observed in vivo are modeled to test for anti-inflammatory activity of different sialic acid enriched and depleted IVIG and Fab fractions.

Many Systemic Lupus Erythematosus (SLE) patients have a Type I "IFN signature" that correlates with disease activity and severity (Bengtsson et al, (2000) Lupus 9(9) 664-671). Immune complexes (ICs) containing RNA or DNA nucleoproteins can be endocytosed to stimulate Toll-like receptors (TLRs 7,9) leading to IFN-α production (Vollmer et al (2005) J. Exp. Med. 2002(11), 1575-1585). In this experiment the goal is to determine if and how sialylated (SA+) IgG modulates IFN-α production after TLR7/TLR9 stimulation of human cells.

Peripheral blood mononuclear cells (PBMCs) were isolated from heparinized venous blood of healthy volunteers by density-gradient centrifugation over Ficoll-Paque (Amersham Biosciences). PBMC cultures ($5 \times 10^5$/well in a 96-well round-bottom tissue culture plate, Nunc, total volume 150 µL) were stimulated with Loxoribine (200 µM, Invivogen) or CpG 2216 (200 nM, Invivogen) and treated with IVIG (enriched or depleted of the sialylated fraction as described in Example 1) or the corresponding F(ab')2 portion at a concentration of 500 µg/ml of IgG or an equimolar amount of F(ab')2 fragments (333 µg/ml F(ab')2). Supernatants were collected after 20±2 h, and IFN-α was quantified by an in-house ELISA using commercially available antibodies as described (Santer et al., (2009) J. Immunol 182, 1192-1201). Results are expressed as the percentage of inhibition of IFN-α relative to cells that did not receive IVIG treatment.

It can be seen that in equimolar concentration the F(ab')2 preparations give the same level of inhibition as their whole IgG counterparts (or perhaps even a bit more inhibition), indicating that it is the Fab portion having an increased sialylation that is responsible for the greater IFN-alpha inhibition.

Example 8

The Effect of Fab Sialylation on in Vitro Anti-Inflammatory Activity, using the Human Monocyte Cell Line U937

U937 cells (ATCC) are grown in culture according to instructions provided by ATCC. The cells are differentiated a day before the experiment with retinoic acid (0.5 µM) and/or Vitamin D.

The differentiated U937 cells are harvested by centrifugation at 400×g and re-suspended with PBS containing 1% human Albumin. The cells are then stimulated with 50 to 500 Units Interferon-gamma (IFNγ) or 0.1 to 2 microgram phytohemagglutinin (PHA). Sialic acid enhanced and depleted IVIG and fragments thereof are added to the cells during the stimulation or prior to the addition of the stimulating agents.

After 20+/−2 h of incubation at 37° C., the stimulation is monitored by measuring inflammatory markers in the supernatant by commercial ELISA kits or Bead Array for human inflammatory cytokines from Becton Dickinson (BD Biosciences). IL-8 and neopterin is measured using ELISA kits (Biosource/Demeditec diagnostics).

Surface markers (CD54, CD14, CD45) are quantified by FACS analysis using fluorescent labelled antibodies (BD Pharmingen) on a BD FACS Cantoll (BD Bioscience).

A reduction of inflammatory markers by the +SA fraction of IVIG and by an equimolar amount of F(ab')2 fragments prepared from the +SA fraction is observed as compared to unfractionated IVIG and corresponding F(ab')2 fragments, indicating the anti-inflammatory properties of the immunoglobulin enriched for increased sialylation in the Fab region.

Example 9

Monocyte Derived Dendritic Cell (moDC) Stimulation Assay

Isolation of Human Monocytes and Differentiation of Immature Monocyte-Derived Dendritic Cells (iMoDCs)

Peripheral Blood Mononuclear Cells (PBMCs) are isolated from buffy coat (Blutspendedienst SRK, Bern, CH), containing the cellular part of the whole blood donation of one donor, by density centrifugation. The buffy coat is 1/1 diluted in PBS. 25 ml of the diluted buffy coat are loaded on 15 ml Ficoll Plaque (GE Healthcare Europe GmbH, Otelfingen, CH) and centrifuged for 35 mins (RT, 400 g, no brakes for stopping). The cell layers containing the PBMCs are collected and pooled. After washing (twice in 50 ml PBS), monocytes are isolated by magnetic cell sorting (MACS) using CD14-MACS beads (Miltenyi Biotech GmbH, Bergisch Gladbach, GER). The correct number of PBMCs (10× the number of monocytes needed) is taken up in MACS buffer (PBS, 0.5% BSA, 2 mM EDTA) and incubated with anti-CD14 mAb-coated MACS beads (80 µl/$10^7$ PBMCs; Miltenyi Biotech GmbH) for 20 mins on ice (dark). After washing with MACS buffer (centrifuged for 10 mins at 200 g), bead-labelled cells are loaded on a pre-washed (3 ml MACS buffer) LS MACS column (Miltenyi Biotech GmbH), washed (3× with 3 ml MACS buffer) and flushed with 5 ml MACS buffer after removing of the column from the magnetic field. After washing with PBS, the freshly isolated monocytes are taken up in RPMI-1640, containing 10% iFCS (Biochrom AG, Berlin, DE), 10'000 U/ml penicillin and streptomycin (Amimed, BioConcept, Allschwil, CH) and 10 mM HEPES, and distributed to 24-well ($0.5 \times 10^6$ monocytes/well (m1j) or 48-well plates ($0.25 \times 106$ monocytes/well (0.5 ml)) (BD Biosciences) at a concentration of $0.5 \times 10^6$ monocytes/ml. The purity of the isolated monocytes is assessed by FACS analysis by CD14 staining. Details of the FACS analysis are described later.

During the following 6 days, the monocytes are differentiated into immature monocyte-derived dendritic cells (iMoDCs) in presence of 50 ng/ml GM-CSF (R&D Systems Europe Ltd., Abingdon, UK) and 20 ng/ml recombinant human IL-4 (PeproTech EC Ltd., London UK). During differentiation, every second day, half of the medium gets removed and replaced by fully supplemented (see above)

fresh medium. After 6 days, the cells are analysed for DC-phenotype by light microscopy and by FACS analysis. Cell surface expression of CD14, DC-SIGN (CD209), CD11c and CD1a (all monoclonal Abs from BD Biosciences) is assessed. Details of the FACS analysis are described later.

FACS Analysis of Freshly Isolated Monocytes, Differentiated iMoDCs and Maturated MoDCs Approximately 60,000-100,000 cells in 50 µl FACS buffer (PBS, 2% iFCS) are stained with 1-2 µl of ready-to-use mAbs (anti-CD14, CD11c, CD1a, DC-SIGN, HLA-DR, CD80, CD86, CD83, CD64, CD32 and CD16; all Abs are directly labelled monoclonal Abs of BD Biosciences) and incubated for 30 mins at 4° C. (dark). The cells are washed with PBS and taken up in 50 µl PBS, fixed in 350 µl 1× BD CellFix (BD Biosciences) and stored in the dark at 4° C. until acquisition. Per sample, 10,000 cells are acquired with a FACS Calibur and analysed by the BD CellQuest software (both BD Biosciences).

Stimulation of iMoDCs by Immune Complexes

Immature (i)MoDCs are pre-incubated for 3 h with different amounts of IVIG fractions and F(ab')$_2$ fragments as indicated. iMoDCs are stimulated with 0.1-100 µg/ml LPS as indicated. 0.5×10$^6$ iMoDCs, differentiated in 24 well plates in fully supplemented RPMI (incl. 50 ng/ml GM-CSF & 20 ng/ml IL-4), are incubated with LPS during 24 hs at 37° C., 5% $CO_2$. For the analysis of IC-mediated stimulation (maturation), FACS analysis and cytokine measurements are performed. The cells are harvested by washing them away from the well bottom via pipetting. The cell suspension is collected and stored on ice immediately. After centrifugation (300 g, 10 mins, 4° C.), the supernatants are collected and stored at −20° C. for later cytokine measurement. The cells are taken up in 50 µl of FACS buffer (PBS, 2% iFCS) and FACS analyses are performed as described above. Cell surface expression of the two co-stimulatory molecules CD80 (B7-1) and CD86 (B7-2) is measured as well as the DC-specific maturation marker CD83 (all directly labelled mAbs, BD Biosciences).

Cytokine Measurements in Cell Culture Supernatants

Cell culture supernatants of the iMoDC-stimulation experiments are collected and stored at −20° C. until cytokine measurement. IL-12p70, IL-10, IL-6, IL-8, TNF-α and IL-1β are measured according to manufacturer's instructions by a Cytometric Bead Array (CBA) for human inflammatory cytokines from Becton Dickinson (BD Biosciences).

A reduction of inflammatory markers by the +SA fraction of IVIG and by an equimolar amount of F(ab')2 fragments prepared from the +SA fraction is observed as compared to unfractionated IVIG and corresponding F(ab')2 fragments, indicating the anti-inflammatory properties of the immunoglobulin enriched for increased sialylation in the Fab region.

Example 10

Assessment of the Beneficial Effect of Sialylated IVIg as Compared to Conventional IVIg in EAE Mouse Model Assessment of anti-inflammatory effects of IVIG+SA can be observed in autoimmune models and the underlying mechanism can be studied. In this model, it is shown that IVIG exerts its anti-inflammatory effects through an expansion of regulatory T cells. Using EAE, a comparison among Sial Fc, sialylated F(ab')$_2$, Sialylated intact IVIg and IVIg is done. Different doses of these preparations are administered from day 0 to the peak of the disease or to day 5. Clinical scores and survival are determined.

Induction of EAE

C57BL/6J strains of mice are used to induce EAE. The experiments are performed in accordance with ethical rules on animal experiments. 10-12 weeks old female mice are immunized with 200 µg $MOG_{35-55}$ peptide (>95% purity) emulsified in CFA (1v/1v) containing 800 µg of non-viable desiccated *Mycobacterium tuberculosis* H37RA. A final volume of 200 µl is injected s.c. at four sites over the flanks. In addition, 300 ng of Pertussis toxin is given i.v. on the same day and two days later. Clinical signs of EAE are assessed daily by means of the following scoring system: 0—no signs; 1—tail paralysis; 2—hindlimb weakness and tail paralysis; 3—hindlimb and tail paralysis; 4—hindlimb and tail paralysis and forelimb weakness; 5—morbidum; 6—death. EAE symptoms are observed from day 10 onwards and peak around 21-25 days post-immunization with an average clinical score of 3.

A reduction of clinical symptoms by the +SA fraction of IVIG and by an equimolar amount of F(ab')2 fragments prepared from the +SA fraction is observed as compared to unfractionated IVIG and corresponding F(ab')2 fragments, indicating the anti-inflammatory properties of the immunoglobulin enriched for increased sialylation in the Fab region.

The invention claimed is:

1. A method of treating an inflammatory condition in a patient in need thereof, comprising administering an immunoglobulin G preparation obtained from blood plasma to the patient,
wherein the preparation is enriched for immunoglobulin G molecules having an increased amount of sialylation, wherein the increase is greater in the Fab region than in the Fc region, as compared to an immunoglobulin G preparation obtained from blood plasma prior to enrichment,
and wherein the inflammatory condition is systemic lupus erythematosus (SLE), antiphospholipid syndrome, Kawasaki disease, a skin blistering disease, dermatomyositis, or polymyositis.

2. The method of claim 1, wherein the immunoglobulin G preparation is for intravenous administration (IVIG) or subcutaneous administration (SCIG).

3. The method of claim 1, wherein the inflammatory condition is SLE.

4. The method of claim 1, wherein the immunoglobulin G preparation is enriched for immunoglobulin G molecules having an increased amount of sialylation in the Fab region by subjecting the immunoglobulin G preparation to chromatography with a *Sambucus nigra* agglutinin affinity chromatography matrix.

5. The method of claim 4, wherein the *Sambucus nigra* agglutinin affinity chromatography matrix is selective for Fab sialylation over Fc sialylation.

6. The method of claim 5, wherein the *Sambucus nigra* agglutinin affinity chromatography is performed at a basic pH at which the matrix selectively binds sialic acid residues in the Fab region of the immunoglobulin G molecules.

\* \* \* \* \*